United States Patent
Luo et al.

(10) Patent No.: US 10,774,387 B2
(45) Date of Patent: Sep. 15, 2020

(54) METHODS FOR IDENTIFYING ANDROGEN RECEPTOR SPLICE VARIANTS IN SUBJECTS HAVING CASTRATION RESISTANT PROSTATE CANCER

(71) Applicant: The Johns Hopkins University, Baltimore, MD (US)

(72) Inventors: Jun Luo, Clarksville, MD (US); Emmanuel S. Antaonarakis, Silver Springs, MD (US); Changxue Lu, Ellicott City, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 143 days.

(21) Appl. No.: 15/309,986

(22) PCT Filed: May 19, 2015

(86) PCT No.: PCT/US2015/031584
§ 371 (c)(1),
(2) Date: Nov. 9, 2016

(87) PCT Pub. No.: WO2015/179404
PCT Pub. Date: Nov. 26, 2015

(65) Prior Publication Data
US 2017/0268063 A1  Sep. 21, 2017

Related U.S. Application Data

(60) Provisional application No. 62/000,263, filed on May 19, 2014.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 4,877,611 A | 10/1989 | Cantrell |
| 5,223,409 A | 6/1993 | Ladner et al. |
| 5,225,539 A | 7/1993 | Winter |
| 5,399,346 A | 3/1995 | Anderson et al. |
| 5,530,101 A | 6/1996 | Queen et al. |
| 5,556,752 A | 9/1996 | Lockhart et al. |
| 5,565,332 A | 10/1996 | Hoogenboom et al. |
| 5,578,832 A | 11/1996 | Trulson et al. |
| 5,585,089 A | 12/1996 | Queen et al. |
| 5,593,839 A | 1/1997 | Hubbell et al. |
| 5,599,695 A | 2/1997 | Pease et al. |
| 5,631,734 A | 5/1997 | Stern et al. |
| 5,693,762 A | 12/1997 | Queen et al. |
| 5,721,367 A | 2/1998 | Kay et al. |
| 5,837,243 A | 11/1998 | Deo et al. |
| 5,837,832 A | 11/1998 | Chee et al. |
| 5,843,708 A | 12/1998 | Hardman et al. |
| 5,859,205 A | 1/1999 | Adair et al. |
| 5,939,598 A | 8/1999 | Kucherlapati et al. |
| 6,113,898 A | 9/2000 | Anderson et al. |
| 6,130,364 A | 10/2000 | Jakobovits et al. |
| 6,180,377 B1 | 1/2001 | Morgan et al. |
| 6,423,511 B1 | 7/2002 | Nakamura et al. |
| 6,436,665 B1 | 8/2002 | Kuimelis |
| 6,458,592 B1 | 10/2002 | Jakobovits et al. |
| 9,146,238 B2 | 9/2015 | Luo et al. |
| 9,387,216 B2 * | 7/2016 | Njar ................. A61K 31/58 |
| 9,671,405 B2 * | 6/2017 | Giannakakou ....... A61K 31/337 |
| 2002/0165381 A1 | 11/2002 | Ahrens-Fath et al. |
| 2007/0248535 A1 | 10/2007 | Buttyan et al. |
| 2013/0130241 A1 * | 5/2013 | Dehm ................. C12Q 1/6886 435/6.11 |
| 2015/0233927 A1 | 8/2015 | Giannakakou et al. |
| 2015/0344965 A1 | 12/2015 | Luo et al. |
| 2017/0275673 A1 | 9/2017 | Luo et al. |

FOREIGN PATENT DOCUMENTS

| | | |
|---|---|---|
| CA | 2721506 A1 | 10/2009 |
| CA | 2959336 A1 | 3/2016 |
| EP | 0721016 A2 | 7/1996 |
| EP | 0728520 A1 | 8/1996 |
| EP | 0785280 A2 | 7/1997 |
| EP | 0799897 A1 | 10/1997 |
| EP | 2300041 A2 | 3/2011 |
| EP | 3062106 A1 | 8/2016 |
| EP | 3186393 A1 | 7/2017 |
| WO | WO-86/01533 | 3/1986 |
| WO | WO-95/22058 A1 | 8/1995 |
| WO | WO-97/02357 A1 | 1/1997 |

(Continued)

OTHER PUBLICATIONS

Jiang et al. (Clin Chem, 2010, 56:9, p. 1492-1495) (Year: 2010).*
Wu et al. (2013, Grant W81XWH-12-1-0267; p. 1-19) (Year: 2013).*
Wang et al. (Nature Reviews Genetics, 2009, vol. 10, p. 57-63) (Year: 2009).*
Sieben et al. (J of Magnetism and Magnetic Materials, 2001, vol. 225, p. 175-179) (Year: 2001).*
Cann, G. M. et al., "mRNA-Seq of Single Prostate Cancer Circulating Tumor Cells Reveals Recapitulation of Gene Expression and Pathways Found in Prostate Cancer" Plos One (2012) 7(11):1-10 e49144.
Cassatella et al., Single circulating tumor cell profiling: a new perspective for targeted therapy?, Future Oncology (2012) ,vol. 8, No. 10, pp. 1253-1256 (Abstract).

(Continued)

*Primary Examiner* — Stephanie K Mummert
(74) *Attorney, Agent, or Firm* — Ballard Spahr LLP

(57) ABSTRACT

Methods of the present disclosure provide for detection of mutations and splice variants of the androgen receptor using a non-invasive approach, RNAseq, for examining circulating tumor cells.

18 Claims, 13 Drawing Sheets

Specification includes a Sequence Listing.

(56) References Cited

FOREIGN PATENT DOCUMENTS

| WO | WO-97/27317 | 7/1997 |
|---|---|---|
| WO | WO-97/29212 A1 | 8/1997 |
| WO | WO-02/17904 | 3/2002 |
| WO | WO-2009/128936 A2 | 10/2009 |
| WO | WO-2012/006241 | 1/2012 |
| WO | WO-2014/018926 A1 | 1/2014 |
| WO | WO-2014/047285 A1 | 3/2014 |
| WO | WO-2014/066864 A2 | 5/2014 |
| WO | WO-2015/023710 A1 | 2/2015 |
| WO | WO-2015/179404 A1 | 11/2015 |
| WO | WO-2016/033114 A1 | 3/2016 |

OTHER PUBLICATIONS

DeBono, J.S. et al., "Circulating tumor cells predict survival benefit from treatment in metastatic castration-resistant prostate cancer". Clin. Cancer Res. (2008) 14(19): 6302-6309.
Dehm, S. M., et al. "Splicing of a novel androgen receptor exon generates a constitutively active androgen receptor that mediates prostate cancer therapy resistance" (2008) Cancer Research 68(13), 5469-5477.
Hu, R., et al. Ligand-independent Androgen Receptor Variants Derived from Splicing of Cryptic Exons Signify Hormone Refractory Prostate Cancer: Cancer Res. (2009); 69(1): 16-22.
Li et al. "Androgen Receptor Splice Variants Mediate Enzalutamide Resistance in Castration-Resistant Prostate Cancer Cell Lines." Cancer Research, (2012), vol. 73, pp. 483-489.
Magbanua, MJ, "Isolation and genomic analysis of circulating tumor cells from castration resistant metastatic prostate cancer" BMC Cancer. (2012) 12:78.
Mortazavi, A., et al., Mapping and quantifying mammalian transcriptomes by RNA-Seq. Nature Methods, (2008) 5(7): 621-628.
Mostaghel et al. "Resistance to CYP17A1 Inhibition with Abiraterone in Castration-Resistant Prostate Cancer: Induction of Steroidogenesis and Androgen Receptor Splice Variants," Clin Cancer Res. (2011); 17(18): 5913-5925.
Prensner et al., Beyond PSA: The Next Generation of Prostate Cancer Biomarkers, ScienceTranslationalMedicine.org (2012) 4(127):1-12.
Ramsköld et al., Full-length mRNA-Seq from single-cell levels of RNA and individual circulating tumor cells Nature Biology (2012) 30(8):777-785.
Robinson, JT, et al. Integrative genomics viewer. Nat Biotechnol. (2011) 29:24-26.
Trapnell C., et al. "TopHat: discovering splice junctions with RNA-Seq." Bioinformatics. (2009) 25(9): 1105-1111.
Trapnell C., et al., "Differential gene and transcript expression analysis of RNA-seq experiments with TopHat and Cufflinks". Nat Protoc. (2012) 7:562-578.
Trapnell, Cole et al "Transcript assembly and quantification by RNA-Seq reveals unannotated transcripts and isoform switching during cell differentiation". Nat Biotechnol (2010) 28(5): 511-515. (Cufflinks).
Wang, Z., M. Gerstein, and M. Snyder, RNA-Seq: a revolutionary tool for transcriptomics. Nat Rev Genet, (2009) 10(1): p. 57-63.
Welty, C. et al., Single cell transcriptomic analysis of prostate cancer cells, BMC Molecular Biology (2013), 14:6.
Yu, M. et al., "Circulating tumor cells: approaches to isolation and characterization". J Cell Biol. (2011); 192(3): 373-382.
International Search Report and Written Opinion dated Sep. 24, 2015 by the International Searching Authority for Application No. PCT/US2015/031584, which was filed on May 19, 2015 and published as WO 2015/179404 on Nov. 26, 2015 (Applicant—The Johns Hopkins University ) (17 pages).
International Preliminary Report on Patentability dated Nov. 22, 2016 by the International Searching Authority for Application No. PCT/US2015/031584, which was filed on May 19, 2015 and published as WO 2015/179404 on Nov. 26, 2015 (Applicant—The Johns Hopkins University ) (13 pages).
Abrahamsson, P.A., Neuroendocrine Cells in Tumor Growth of the Prostate, Endocrine-Related Cancer, 6:503-19 (1999).
Agoulnik, I.U. and N.L. Weigel, Androgen Receptor Action in Hormone-Dependent and Recurrent Prostate Cancer, J Cell BioChem, 99:362-72 (2006).
Anders et al., HTSeq—A Python framework to work with high-throughput sequencing data, Bioinformatics (doi: 10.1093/bioinformatics/btu638) (2014).
Andersen et al., Regression of castrate-recurrent prostate cancer by a small-molecule inhibitor of the amino-erminus domain of the androgen receptor. Cancer cell 2010; 17:535-46.
Anderson, W.F., Prospects for Human Gene Therapy, Science, 226(4673):401-9 (1984).
Antonarakis, E.S. et al: AR-V7 and resistance to enzalutamide and abiraterone in prostate cancer. N Engl J Med 371: 1028-1038, 2014.
Armstrong AI, et al. Biomarkers in the management and treatment of men with metastatic castration-resistant prostate cancer. Eur Urol 61: 549-59, 2012.
Armstrong, A.J. and M.A. Carducci, New Drugs in Prostate Cancer, Curr Opin Urol, 16:138-45 (2006).
Arora VK, et al. Glucocorticoid receptor confers resistance to antiandrogens by bypassing androgen receptor blockade. Cell 2013; 155:1309-22.
Aryee et al. DNA methylation alterations exhibit intraindividual stability and interindividual heterogeneity in prostate cancer metastases. Science translational medicine 2013;5:169ra10.
Attard et al. Phase I clinical trial of a selective inhibitor of CYP17, abiraterone acetate, confirms that castration-resistant prostate cancer commonly remains hormone driven. Journal of clinical oncology: official journal of the American Society of Clinical Oncology 2008; 26:4563-71.
Balbas et al. Overcoming mutation-based resistance to antiandrogens with rational drug design. eLife 2013;2.
Balic et al., Androgen Receptor Length Polymorphism Associated with Prostate Cancer Risk in Hispanic Men, J Urol, 168(5): 2245-8 (2002).
Barltrop, J.A. et al., 5-(3-Carboxymethoxyphenyl)-2-(4,5-Dimethylthiszolyl)-3-(4-Sulfophenyl)Tetrazolium, Inner salt (MTS) and Related Analogs of 3-(4,5-Dimethylthiazolyl)-2,5-Diphenyltetrazolium Bromide (MTT) Reducing to Purple Water-Soluble Formazans as Cell-Viability Indicators, Bioorg & Med Chem Lett, 1(11): 611-4 (1991).
Basch E, et al: Systemic therapy in men with metastatic castration-resistant prostate cancer: American Society of Clinical Oncology and Cancer .Care Ontario clinical practice guideline. J Clin Oncol 32: 3436-3448, 2014.
Bendig, M.M., Humanization of Rodent Monoclonal Antibodies by CDR Grafting, Methods: A Companion Methods in Enzymology, 8:83-93 (1995).
Blömer, U. et al., Highly Efficient and Sustained Gene Transfer in Adult Neurons with a Lentivirus Vector, J Virology, 71(9): 6641-9 (1997).
Brigham, K.L. et al., In Vivo Transfection of Murine Lungs with a Functioning Prokaryotic Gene Using a Liposome Vehicle, Am J Med Sci, 298(4): 278-81 (1989).
Brinkmann, A.O. et al., Mechanisms of Androgen Receptor Activation and Function, J Steroid Biochem Mol Biol, 69(1-06): 307-13 (1999).
Brown et al., Deletion of the Steroid-Binding Domain of the Human Androgen Receptor Gene in One Family with Complete Androgen Insensitivity Syndrome: Evidence for Further Genetic Heterogeneity in this Syndrome, Proc Natl Acad Sci USA, 85(21): 8151-5 (1988).
Butler, L.M. et al., Suppression of Androgen Receptor Signaling in Prostate Cancer Cells by an Inhibitory Receptor Variant, Mol Endocrinol, 20(5): 1009-24 (2006).
Carell, T. et al., A Novel Procedure for the Synthesis of Libraries containing Small Organic Molecules, Angew Chem Int Ed Engl, 33(20): 2059-61 (1994).

(56) References Cited

OTHER PUBLICATIONS

Carell, T. et al., A Solution-Phase Screening Procedure for the Isolation of Active Compounds from a Library of Molecules, Angew Chem Int Ed Engl, 33(20): 2061-4 (1994).

Carver et al. Reciprocal feedback regulation of PI3K and androgen receptor signaling in PTEN-deficient prostate cancer. Cancer cell 2011; 19:575-86.

Casset, F. et al., A Peptide Mimetic of an Anti-CD4 Monoclonal Antibody by Rational Design, Biochem Biophys Res Commun, 307(1): 198-205 (2003).

Catalano, M.G. et al., Altered Expression of Androgen-Receptor Isoforms in Human Colon-Cancer Tissues, Intl J Cancer, 86(3): 325-30 (2000).

Cayouette, M. and C. Gravel, Adenovirus-Mediated Gene Transfer of Ciliary Neurotrophic Factor Can Prevent Photoreceptor Degeneration in the Retinal Degeneration (rd) Mouse, Human Gene Therapy, 8:423-30 (1997).

Chang, K. H., et al. A Gain-of-Function Mutation in DHT Synthesis in Castration-Resistant Prostate Cancer. (2013) Cell 154, 1074-1084.

Chee et al., Accessing Genetic Information with High-Density DNA Arrays. Science 274:610 (1996).

Chen, C.D. et al., Molecular Determinants of Resisteance to Antiandrogen Therapy, Nature Med, 10(1): 33-9 (2004).

Chen, Y. et al., Targeting the Androgen Receptor Pathway in Prostate Cancer, Curr Opin Pharm, 8: 440-8 (2008).

Chmelar, R. et al., Androgen Receptor Coregulators and Their Involvement in the Development and Progression of Prostate Cancer, Int J Cancer, 120: 719-33 (2006).

Cho, C.Y. et al., An Unnatural Biopolymer, Science, 261(5126): 13303-5 (1993).

Cordon-Cardo, C., Androgen Receptor Level in the Prostatectomy Specimen Predicts Time to Disease Progression Post Androgen Suppression Therapy, J Clin Oncol, 25(18S): 5065 (2007).

Cornetta, K. et al., Gene Transfer into Primates and Prospects for Gene Therapy in Humans, Prog Nucleic Acid Res Mol Biol, 36: 311-22 (1989).

Cory, A.H. et al., Use of an Aqueous Soluble Tetrazolium/Formazan Assay for Cell Growth Assays in Culture, Cancer Commun, 3(7): 207-12 (1991).

Cree, A.I. et al., Methotrexate Chemosensitivity by ATP Luminescence in Human Leukemia Cell Lines and in Breast Cancer Primary Cultures: Comparison of the TCA-100 Assay with a Clonogenic Assay, Anticancer Drugs, 6(3): 398-404 (1995).

Crouch, S.P.M., et al., The Use of ATP Bioluminescence as a Measure of Cell Proliferation and Cytotoxicity, J Immunol Meth, 160: 81-8 (1993).

Cull, M.G. et al., Screening for Receptor Ligands Using Large Libraries of Peptides Linked to the C Terminus of the Iac Repressor, Proc Natl Acad Sci USA, 89: 1865-9 (1992).

Cwirla, S.E., et al., Peptides on Phage: A Vast Library of Peptides for Identifying Ligands, Proc Natl Acad Sci USA, 87: 6378-82 (1990).

Céraline, J. et al., Constitutive Activation of the Androgen Receptor by a Point Mutation in the Hinge Region: A New Mechanism for Androgen-Independent Growth in Prostate Cancer, Int J Cancer, 108:152-7 (2004).

Darshan, et al., Taxane-induced blockade to nuclear accumulation of the androgen receptor predicts clinical responses in metastatic prostate cancer. Cancer Res 71: 6019-6029, 2011.

De Bono, JS et al: Abiraterone and increased survival m metastatic prostate cancer. N Engl J Med 364: 1995-2005, 2011.

De Bono, JS et al., Prednisone plus cabazitaxel or mitoxantrone for metastatic castration-resistant prostate cancer progressing after docetaxel treatment: a randomised open-label trial: Lancet 376: 1147-1154, 2010.

De Leeuw et al., Novel actions of next-generation taxanes benefit advanced stages of prostate cancer. Clin. Cancer Res. 2015; 21:795-807.

Dehm, S.M. and D.J. Tindall, Androgen Receptor Structural and Functional Elements: Role and Regulation in Prostate Cancer, Mol Endocrinol, 21(12): 2855-63 (2007).

Devlin, J.J. et al., Random Peptide Libraries: A Source of Specific Protein Binding Molecules, Science, 249(4967): 404-6 (1990).

DeWitt, S.H. et al., "Diversomers:" An Approach to Nonpeptide, nonoligometric Chemical Diversity, Proc Natl Acad Sci USA, 90: 6909-13 (1993).

Dhanasekaran, S.M. et al., Delineation of Prognostic Biomarkers in Prostate Cancer, Nature, 412: 822-6 (2001).

Efstathiou, E. et al., Effects of abiraterone acetate on androgen signaling in castrate-resistant prostate cancer in bone. Journal of clinical oncology : official journal of the American Society of Clinical Oncology 2012;30:637-43.

Efstathiou, E. et al., MDV3100 effects on androgen receptor (AR) signaling and bone marrow testosterone concentration modulation: Apreliminary report. ASCO Meeting Abstracts 2011; 29:4501.

Eisenhauer, E.A. et al:, New response evaluation criteria in solid tumours: revised RECIST guideline (version 1.1). Eur J Cancer 45: 228-247, 2009.

Erb, E. et al., Recursive Deconvolution of Combinatorial Chemical Libraries, Proc Natl Acad Sci USA, 91: 11422-6 (1994).

Feigner, P.L. et al., Lipofection: A Highly Efficient, Lipid-Mediated DNA-Transfection Procedure, Proc Natl Acad Sci USA, 84: 7413-7 (1987).

Felici, F. et al., Selection of Antibody Ligands from a Large Library of Oligopeptides Expressed on a Multivalent Exposition Vector, J Mol Biol, 222: 301-10 (1991).

Fleming, M.T. et al., Post-Therapy Changes in PSA as an Outcome Measure in Prostate Cancer Clinical Trials, Nat Clin Pract Oncol, 3(12): 658-67 (2006).

Fodor, S.P.A. et al., Multiplexed Biochemical Assays with Bilogical Chips, Nature, 364: 555-6 (1993).

Friedmann, T., Progress Toward Human Gene Therapy, Science, 244(4910) 1275-81 (1989).

Gallop, M.A. et al., Applications of Combinatorial Technologies to Drug Discovery. 1. Background and Peptide Combinatorial Libraries, J Med Chem, 37(9): 1233-51 (1994).

Gan, L. et al., Inhibition of the androgen receptor as a novel mechanism of taxol chemotherapy in prostate cancer. Cancer Res 69: 8386-8394, 2009.

Ge, H. Upa, A Universal Protein Array System for Quantitative Detection of Protein-Protein, Protein-DNA, Protein-RNA and Prtein-Ligand Interactions, Neucleic Acids Reseach, 28(2): e3i-vii (2000).

Gelmann, E.P., Molecular Biology of the Androgen Receptor, J Clin Oncol, 20(13): 3001-15 (2002).

Gu, Y. et al., Hematopoietic Cell Regulation by Rac1 and Rac2 Guanosine Triphosphatases, Science, 302: 445-9 (2003).

Guo, Z. et al., A Novel Androgen Receptor Splice Variant Is Up-regulated during Prostate Cancer Progression and Promotes Androgen Depletion-Resistant Growth. Cancer Research 2009; 69:2305-13.

Haapala, K. et al., Androgen receptor alterations in prostate cancer relapsed during a combined androgen blockade byorchiectomy and bicalutamide, Laboratory Investigation, Nature Publishing Group, The United States andCanadian Academy of Pathology, Inc,vol. 81, No. 12, Dec. 2001,pp. 1647-1651.

Hacia et al., Detection of heterozygous mutations in BRCA1 using high density oligonucleotide arrays and two-colour fluorescence analysis. Nature Genetics 14:441, 1996.

Hara, T. et al., Novel mutations of androgen receptor: a possible mechanism of bicalutamide withdrawal syndrome, Cancer Research, American Association for Cancer Research, vol. 63, No. 1, Jan. 2003, pp. 149-153.

Heinlein, C.A. and Chawnshang Chang, Androgen Receptor in Prostate Cancer, Endocr Rev, 25(2): 276-308 (2004).

Heller, R.A. et al., Discovery and Analysis of Inflammatory Disease-Related Genes Using cDNA Microarrays, Proc Natl Acad Sci USA, 94:2150-5 (1997).

Hirata, S. et al., Isoform/Variant mRNAs for Sex Steroid Hormone Receptors in Humans, Trends Endocrin Met, 14(3): 124-9 (2003).

(56) References Cited

OTHER PUBLICATIONS

Hornberg, E. et al., Expression of Androgen Receptor Splice Variants in Prostate Cancer Bone Metastases is Associated with Castration-Resistance and Short Survival. PLoS ONE 2011;6:e19059.
Houghten, R.A. et al., The Use of Synthetic Peptide Combinatorial Libraries for the Identification of Bioactive Peptides, Biotechniques, 13(3): 412-21 (1992).
Hu, R. et al., A snapshot of the expression signature of androgen receptor splicing variants and their distinctive transcriptional activities. The Prostate 2011; 71:1656-67.
Hu, R. et al., Distinct transcriptional programs mediated by the ligand-dependent full-length androgen receptor and its splice variants in castration-resistant prostate cancer. Cancer Res 2012; 72:3457-62.
Huggins, M.D., C. and C.V. Hodges, M.D., Studies on Prostatic Cancer: I. The Effect of Castraction, of Estrogen and of Androgen Injection on Serum Phosphates in Metastatic Carcinoma of the Prostate, Cancer Res, 1: 293-7 (1941).
Itakura et al., Synthesis and Use of Synthetic Oligonucleotides. Ann. Rev. Biochem. 53:323-356 (1984).
Jagla, M. et al., A Splicing Variant of the Androgen Receptor Detected in a Metastatic Prostate Cancer Exhibits Exclusively Cytoplasmic Actions, Endocrin, 148(9): 4334-4343 (2007).
Jenster, G. et al., Domains of the Human Androgen Receptor Involved in Steroid Binding Transcriptional Activation and Subcellular Localization, Mol Endocrin, 5(10): 1396-1404 (1991).
Johnson, L.G., Gene Therapy for Cystic Fibrosis, Chest, 107: 77S-83S (1995).
Joseph, J.D. et al., A clinically relevant androgen receptor mutation confers resistance to 2nd generation anti-androgens enzalutamide and ARN-509. Cancer Discovery 2013.
Kaarbo, Mari et al., Androgen Signaling and Its Interactions with Other Signaling Pathways in Prostate Cancer, BioEssays, 29: 1227-38 (2007).
Kangas, L. et al., Bioluminescence of Cellular ATP: A New Method for Evaluating Cytotoxic Agents in Vitro, Med Biol, 62(6): 338-43 (1984).
Kantoff et al., Sipuleucel-T immunotherapy for castration-resistant prostate cancer. N Engl J Med 363: 411-422, 2010.
Karantanos, T. et al., Understanding the mechanisms of androgen deprivation resistance in prostate cancer at the molecular level. Eur Urol, epub ahead of print (doi: 10.1016/j.eururo.2014.09.049), 2014.
Kido, M. et al., Use of a Retroviral Vector with an Internal Opsin Promoter to Direct Gene Expression to Retinal Photorecptor Cells, Curr Eye Res, 15(8): 833-44 (1996).
Kirby, B.J. et al., Functional characterization of circulating tumor cells with a prostate-cancer-specific microfluidic device. PLoS One 7: e35976, 2012.
Kittler, R. et al., An Endoribonuclease-Prepared siRNA Screen in Human Cells Identifies Genes Essential for Cell Division, Nature, 432: 1036-40 (2004).
Ko et al., Androgen Receptor Down-Regulation in Prostate Cancer with Phosphorodiamidate Morpholino Antisense Oligomers, J Urol, 172(3): 1140-4 (2004).
Kozal et al., Extensive polymorphisms observed in HIV-1 Glade B protease gene using high-density oligonucleotide arrays. Nature Medicine 2:753, 1996.
Lam, K.S., Application of Combinatorial Library Methods in Cancer Research and Drug Discovery, Anticancer Drug Des, 12(3): 145-67 (1997).
Lam, K.S. et al., A New Type of Synthetic Peptide Library for Identifying Ligand-Binding Activity, Nature, 354:82-4 (1991).
Lapouge Gaelle et al., Specific properties of a C-terminal truncated androgen receptor detected in hormone refractory prostate cancer, Advances in Experimental Medicine and Biology, vol. 617, Jan. 2008 pp. 529-534.
Le Gal La Salle, G. et al., An Adenovirus Vector for Gene Transfer into Neurons and Glia in the Brain, Science, 259(5097: 988-90 (1993).
Libertini, S.J. et al., Evidence for Calpain-Mediated Androgen Receptor Cleavage as a Mechanism for Androgen Independence, Cancer Res, 67(19): 9001-5 (2007).
Linja, M.J. and Tapio Visakorpi, Alterations of Androgen Receptor in Prostate Cancer, J Steriod Biochem, 92: 255-64 (2004).
Liu, W. et al., Copy number analysis indicates monoclonal origin of lethal metastatic prostate cancer. Nature medicine 2009; 15:559-65.
Lockhart, D.J. et al., Expression Monitoring by Hybridization to High-Density Oligonucleotide Arrays, Nat Biotechnol, 14: 1675-80 (1996).
Longo, D.L., New therapies for castration-resistant prostate cancer. The New England journal of medicine 2010; 363:479-81.
Luo, J. et al., Human Prostate Cancer and Benign Prostatic Hyperplasia: Molecular Dissection by Gene Expression Profiling, Cancer Res, 61: 4683-8 (2001).
MacBeath, G. and S.L. Schreiber, Printing Proteins as Microarrays for High-Throughput Function Determination, Science, 289: 1760-3 (2000).
MacCallum, R.M. et al., Antibody-Antigen Interactions: Contact Analysis and Binding Site Topography, J Mol Biol, 262(5): 732-45 (1996).
Maroni, M.D., P.D. and E.D. Crawford, M.D., The Benefits of Early Androgen Blockade, Best Pract Res Cl En, 22(2): 317-29 (2008).
Miller, A.D. and G.J. Rosman, Improved Retroviral Vectors for Gene Transfer and Expression, Biotechniques, 7(9): 980-990 (1989).
Miller, A.D., Retrovirus Packaging Cells, Human Gene Therapy, 1:5-14 (1990).
Mitsiades, N. et al., Distinct patterns of dysregulated expression of enzymes involved in androgen synthesis and metabolism in metastatic prostate cancer tumors. Cancer Res 2012; 72:6142-52.
Miyamoto, A. et al., Increased Proliferation of B Cells and Auto-Immunity in Mice Lacking Protein Kinase Cd, Nature, 416: 865-9 (2002).
Miyoshi, H. et al., Stable and Efficient Gene Transfer into the Retina Using an HIV-Based Lentiviral Vector, Proc Natl Acad Sci USA, 94: 10319-23 (1997).
Moen, R.C., Directions in Gene Therapy, Blood Cells, 17(2): 407-16 (1991).
Montgomery, R.B. et al., Maintenance of Intratumoral Androgens in Metastatic Prostate Cancer: A Mechanism for Castration-Resistant Tumor Growth, Cancer Res, 68(11): 4447-54 (2008).
Mostaghel, E.A. and P.S. Nelson, Intracrine Androgen Metabolism in Prostate Cancer Progression: Mechanisms of Castration Resistance and Therapeutic Implications, Best Pract Res Cl En, 22(2): 243-58 (2008).
Nadiminty, N. et al., NF-kappaB2/p52 induces resistance to enzalutamide in prostate cancer: role of androgen receptor and its variants. Molecular cancer therapeutics 2013;12:1629-37.
Naldini, L. et al., In Vivo Gene Delivery and Stable Transduction of Nondividing Cells by a Lentiviral Vector, Science, 272(5259): 263-7 (1996).
Narang et al., Chemical Synthesis of Deoxyoligonucleotides by the Modified Triester Method. Methods Enzymol., 65:610-620 (1980).
Norris, J.D. et al., The homeodomain protein HOXB13 regulates the cellular response to androgens. Molecularcell 2009; 36:405-16.
O'Donnell, A. et al., Hormonal impact of the 17alphahydroxylase/C(17,20)-lyase inhibitor abiraterone acetate (CB7630) in patients with prostate cancer. British journal of cancer 2004;90:2317-25.
Ono, T. et al., Plasmid DNAs Directly Injected into Mouse Brain with Lipofectin can be Incorporated and Expressed by Brain Cells, Neurosci Lett, 117:259-63 (1990).
Otto, D. and K. Unsicker, Basic FGF Reverses Chemical and Morphological Deficits in the Nigrostriatal System of MPTP-Treated Mice, J Neurosci, 10(6): 1912-21 (1990).
Otto, D. et al., Basic Fibroblast Growth Factor and Nerve Growth Factor Administered in Gel Foam Rescue Medial Septal Neurons after Fimbria Fornix Transection, J Neurosci Res, 22(1): 83-91 (1989).
Pan, Q. et al., Quantitative Microarray Profiling Provides Evidence Against Widespread Coupling of Alternative Splicing with Nonsense-Mediated mRNA Decay to Control Gene Expression, Genes & Dev, 20:153-8 (2006).

(56) References Cited

OTHER PUBLICATIONS

Parker, C. et al., Alpha emitter radium-223 and survival m metastatic prostate cancer. N Engl J Med 369: 213-223, 2013.
Paul, W.E., Fundamental Immunology, 3rd Edition, New York: Raven Press, pp. 292-295 (1993).
Paull, K.D. et al., The Synthesis of XTT: A New Tetrazolium Reagent that is Bioreducible to a Water-Soluble Formazan, J Heterocyclic Chem, 25: 911-4 (1988).
Petty, R.D., Comparison of MTT and ATP-Based Assays for the Measurement of Viable Cell Number, J Biolumin Chemilumin, 10:29-34 (1995).
Plymate Sr, et al., Taxane resistance in prostate cancer mediated by ARdependent GATA2 regustion ofIGF2. Cancer Cell, 2015; 27:158-159.
Quigley, C.A. et al., Complete Androgen Insensitiveity due to Deletion of Exon C of the Androgen Receptor Gene Highlights the Functional Importance of the Second Zinc Finger of the Androgen Receptor In Vivo, Mol Endocrinol, 6(7): 1103-12 (1992).
Ravindranathan, P. et al., Peptidomimetic targeting of critical androgen receptor-coregulator interactions in prostate cancer. Nat Commun 2013;4:1923.
Roberts et al., RNA-peptide fusions for the in vitro selection of peptides and proteins. Proc. Natl. Acad. Sci. USA, 94(23)12997-302 (1997).
Rosenberg, S.A. et al., Gene Transfer into Humans—Immunotherapy of Patients with Advanced Melanoma, Using Tumor-Infiltrating Lymphocytes Modified by Retroviral Gene Transduction, New Engl J Med, 323(9): 570-8 (1990).
Ruefli-Brasse, A.A. et al., Regulation of NF-κB-Dependent Lymphocyte Activation and Development by Paracaspase, Science, 302: 1581-4 (2003).
Ryan, C. J. et al., Androgen Receptor Rediscovered: The New Biology and Targeting the Androgen Receptor Therapeutically (2011) Journal of Clinical Oncology: Official Journal of the American Society of Clinical Oncology 29, 3651-3658.
Ryan, C. J., et al. Abiraterone in Metastatic Prostate Cancer without Previous Chemotherapy (2013) New England Journal of Medicine 368, 138-148.
Sadar D.m Small Molecule Inhibitors Targeting the "Achilles' Heel" of Androgen Receptor Activity. (2011) Cancer Res 71, 1208-1213.
Sahu, B. et al., FoxA1 Specifies Unique Androgen and Glucocorticoid Receptor Binding Events in Prostate Cancer Cells (2013) Cancer Res 73, 1570-1580.
Saramäki, O.R. et al., Genetic Aberrations in Prostate Cancer by Microarray Analysis, Int J Cancer, 119: 1322-9 (2006).
Schena, M. et al., Parallel Human Genome Analysis: Microarray-Based Expression Monitoring of 1000 Genes, Proc Natl Acad Sci USA, 93: 10614-9 (1996).
Scher, HI. et al., Design and end points of clinical trials for patients with progressive prostate cancer and castrate levels of testosterone: recommendations of the Prostate Cancer Clinical Trials Working Group. J Clin Oncol 26: 1148-1159, 2008.
Scher, H.I. et al., Increased survival with enzalutamide in prostate cancer after chemotherapy. N Engl J Med 367: 1187-1197, 2012.
Scher, H. I. et al., Antitumour activity of MDV3100 in castration-resistant prostate cancer: A phase 1-2 study (2010) Lancet 375, 1437-1446.
Scher, H.I. and C.L. Sawyers, Biology of Progressive, Castration-Resistant Prostate Cancer: Directed Therapies Targeting the Androgen-Receptor Signaling Axis, J Clin Oncol, 23(32): 8253-61 (2005).
Scott, J.K. and G.P. Smith, Searching for Peptide Ligands with an Epitope Library, Science, 249(4967): 386-90 (1990).
Seruga, B. et al., Drug resistance in metastatic castration-resistant prostate cancer. Nat Rev Clin Oncol 8: 12-23, 2011.
Shang, Y. et al., Formation of the Androgen Receptor Transcription Complex, Mol Cell, 9: 601-10 (2002).
Sharp, D., Conference: Gene Therapy, The Lancet, 337: 1277-8 (1991).

Skolnick, J. and J.S. Fetrow, From Genes to Protein Structure and Function: Novel Applications of Computational Approaches in the Genomic Era, Trends Biotechnol, 18(1): 34-9 (2000).
Small, E.J. and C.J. Ryan, The Case for Secondary Hormonal Therapies in the Chemotherapy Age, J Urol, 176: S66-71 (2006).
Steplewski et al., Effects of Restraint Stress on Inoculated Tumor Growth and Immune Response in Rats. (1985) Cancer Research 45: 5128-5133.
Straubinger, R.M. and D. Papahadjopoulos, Liposomes as Carriers for Intracellular Delivery of Nucleic Acids, Method Enzymol, 101: 512-27 (1983).
Subramanan, A. et al., Gene set enrichment analysis: A knowledge-based approach for interpreting genome-wide expression profiles. (2005) Proceedings of the National Academy of Sciences of the United States of America 102: 15545-15550.
Suzuki, H. et al., Interfocal Heterogeneity of PTEN/MMAC1 Gene Alterations in Multiple Metastatic Prostate Cancer Tissues, Cancer Res, 58: 204-9 (1998).
Tannock, I.F. et al., Docetaxel plus prednisone or mitoxantrone plus prednisone for advanced prostate cancer. N Engl J Med 3 51: 1502-1512, 2004.
Tepper, C.G. et al., Characterization of a Novel Androgen Receptor Mutation in a Relapsed CWR22 Prostate Cancer Xenograft and Cell Line, Cancer Res, 62: 6606-14 (2002).
Thadani-Mulero et al., Androgen receptor on the move: boarding the microtubule expressway to the nucleus. Cancer Res 72: 4611-4615, 2012.
Thadani-Mulero et al., Androgen receptor splice variants determine taxane sensitivity in prostate cancer. Cancer Res 74: 2270-82, 2014.
Therasse P. et al., New Guidelines to Evaluate the Response to Treatment in Solid Tumors. (2000) Journal of the National Cancer Institute 92, 205-216).
Tilley, W.D. et al., Mutations in the Androgen Receptor Gene Are Associated with Progression of Human Prostate Cancer to Androgen Independence , Clin Cancer Res, vol. 2, Jan. 1996, pp. 277-285.
Tolstoshev, P. and W.F. Anderson, Gene Expression Using Retroviral Vectors, Curr Opin Biotech, 1:55-61 (1990).
Tran, C. et al., Development of a Second-Generation Antiandrogen forTreatment of Advanced Prostate Cancer. Science 2009; 324:787-90.
Tyagi, S. and F.R. Kramer, Molecular Beacons: Probes that Fluoresce Upon Hybridization, Nat Biotechnol, 14: 303-8 (1996).
Vajdos, F.F. et al., Comprehensive Functional Maps of the Antigen-Binding Site of an Anti-ErbB2 Antibody Obtained with Shotgun Scanning Mutagenesis, J Mol Biol, 320(2): 415-28 (2002).
Van Soest, R.J. et al., Targeting the androgen receptor confers in vivo cross-resistance between enzalutamide and docetaxel, but not cabazitaxel, in castration-resistant prostate cancer. Eur. Urol. 2014; epub ahead of print (10.1016/j.euro.2014.11.033).
Verhoeyen et al., Engineering of Antibodies. (1988) BioEssays. 8, 2:74-78.
Wahl, R.L. et al., Improved Radioimaging and Tumor Localization with Monoclonal F(ab')2, J Nucl Med, 24: 316-25 (1983).
Watson, P.A., et al., Constitutively active androgen receptor splice variants expressed in castration-resistant prostate cancer require full-length androgen receptor. (2010) Proceedings of the National Academy of Sciences 107 (39):16759-16765.
Wolff, J.A. et al., Direct Gene Transfer into Mouse Muscle in Vivo, Science, 247(4949 pt. 1): 1465-8 (1990).
Wu, C.H. et al., Targeting Genes: Delivery and Persistent Expression of a Foreign Gene Driven by Mammalian Regulatory Elements in Vivo, J Biol Chem, 264(29): 16985-7 (1989).
Wu, G.Y. and C.H. Wu, Receptor-Mediated Gene Delivery and Expression in Vivo, J Biol Chem, 263(29): 14621-4 (1988).
Wu, H. et al., Humanization of a murine monoclonal antibody by simultaneous optimization of framework and CDR residues, J Mol Biol, 294(1): 151-62 (1999).
Yu et al., Rapid Induction of Androgen Receptor Splice Variants by Androgen Deprivation in Prostate Cancer. Clin Cancer Res. 2014, vol. 20, No. 6, ; pp. 1590-1600.

(56) References Cited

OTHER PUBLICATIONS

Yu, Y. et al., Expression and Function of the Progesterone Receptor in Human Prostate Stroma Provide Novel Insights to Cell Proliferation Control (2013) The Journal of clinical endocrinology and metabolism 98, 2887-2896.
Zhang, X. et al., Androgen Receptor Variants Occur Frequently in Castration Resistant Prostate Cancer Metastases. (2011) PLoS ONE 6, e27970.
Zhou, Z. et al., A Ligand-Dependent Bipartite Nuclear Targeting Signal in the Human Androgen Receptor, J Biol Chem, 269(18): 13115-23 (1994).
Zhu et al., Tubulin-targeting chemotherapy lmpairs androgen receptor activity in prostate cancer. Cancer Res 70: 7992-8002, 2010.
Zhu, H. et al., Analysis of Yeast Protein Kinases Using Protein Chips, Nat Genet, 26: 283-9 (2000).
Zhu, X. et al., Identification of an Exon 3 Deletion Splice Variant Androgen Receptor mRNA in Human Breast Cancer, Intl J Cancer, 72(4): 574-80 (1997).
Zuckermann, R.N. et al., Discovery of Nanomolar Ligands for 7-Transmembrane G-Protein-Coupled Receptors from a Diverse N-(Substituted)glycine Peptoid Library, J Med Chem, 37: 2678-85 (1994).
Communication Pursuant to Rules 161(2) and 162 EPC dated Mar. 31, 2017 by the European Patent Office for Patent Application No. 15835018.1, which was filed on Aug. 25, 2015 and published as 3186396 on Jul. 5, 2017 (Inventor—Luo et al.; Applicant—Johns Hopkins University) (2 pages).
International Search Report and Written Opinion dated Jan. 12, 2016 by the International Searching Authority for International Application No. PCT/US2015/046806, which was filed on Aug. 25, 2015 and published as WO/2016/033114 on Mar. 3, 2016 (Applicant—The John Hopkins University) (13 pages).
International Preliminary Report on Patentability dated Feb. 28, 2017 by the International Searching Authority for International Application No. PCT/US2015/046806, which was filed on Aug. 25, 2015 and published as WO/2016/033114 on Mar. 3, 2016 (Applicant—The John Hopkins University) (9 pages).
Preliminary Amendment filed on Feb. 22, 2017 by the United States Patent and Trademark Office for U.S. Appl. No. 15/505,882, filed Feb. 22, 2017 (Inventor—Luo et al.; Applicant—The Johns Hopkins University) (11 pages).
Office Action dated Apr. 30, 2015 by the Canadian Intellectual Property Office for Patent Application No. 2721506, which was filed on Apr. 16, 2009 (Inventor—Luo et al.; Applicant—The Johns Hopkins University) (9 pages).
Office Action dated May 24, 2017 by the Canadian Intellectual Property Office for Patent Application No. 2721506, which was filed on Apr. 16, 2009 (Inventor—Luo et al.; Applicant—The Johns Hopkins University) (7 pages).
Supplementary European Search Report and Written Opinion completed on Jul. 26, 2011 by the European Patent Office for European Patent Application No. 09733012.0, which was filed on Apr. 16, 2009 and published as 2300041 on Mar. 30, 2011 (Inventor—Luo et al.; Applicant—The Johns Hopkins University) (10 pages).
Certificate of Patent issued on Jan. 27, 2016 by the European Patent Office for European Patent Application No. 0933012.0, which was filed on Nov. 15, 2010 and granted as 2300041 on Mar. 30, 2011 (Inventor—Luo et al.; Applicant—The Johns Hopkins University) (1 page).
European Search Report and Written Opinion completed on Jun. 6, 2016 by the European Patent Office for European Patent Application No. 16152616.5, which was filed on Apr. 16, 2009 and published as 3062106 on Aug. 31, 2016, 2011 (Inventor—Luo et al.; Applicant—The Johns Hopkins University) (9 pages).
Communication Pursuant to Article 94(3) EPC dated Aug. 18, 2017 by the European Patent Office for European Patent Application No. 16152616.5, which was filed on Apr. 16, 2009 and published as 3062106 on Aug. 31, 2016, 2011 (Inventor—Luo et al.; Applicant—The Johns Hopkins University) (4 pages).
International Search Report and Written Opinion dated Dec. 4, 2009 by the International Searching Authority for International Patent Application No. PCT/US2009/002392, which was filed on Apr. 6, 2009 and published as WO 2009/128936 on Oct. 22, 2009 (Inventor—Luo et al.; Applicant—The Johns Hopkins University) (11 pages).
International Preliminary Report on Patentability dated Oct. 19, 2010 by the International Searching Authority for International Patent Application No. PCT/US2009/002392, which was filed on Apr. 6, 2009 and published as WO 2009/128936 on Oct. 22, 2009 (Inventor—Luo et al.; Applicant—The Johns Hopkins University) (8 pages).
Preliminary Amendment filed on Oct. 15, 2010 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (11 pages).
Restriction Requirement dated Feb. 29, 2012 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (8 pages).
Response to Restriction Requirement filed on Mar. 29, 2012 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (4 pages).
Non-Final Office Action dated Jun. 20, 2012 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (5 pages).
Response to Non-Final Office Action filed on Sep. 20, 2012 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (12 pages).
Final Office Action dated Sep. 12, 2013 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (5 pages).
Response to Final Office Action filed on Dec. 12, 2013 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (9 pages).
Advisory Action dated Dec. 19, 2013 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (3 pages).
Non-Final Office Action dated Jun. 5, 2014 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (9 pages).
Response to Non-Final Office Action filed on Aug. 7, 2014 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (10 pages).
Final Office Action dated Nov. 21, 2014 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (21 pages).
Response After Final Office Action filed on Mar. 3, 2015 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (8 pages).
Advisory Action dated Apr. 9, 2015 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (5 pages).
Response to Advisory Action filed on Apr. 19, 2015 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (6 pages).

(56) References Cited

OTHER PUBLICATIONS

Advisory Action dated Apr. 28, 2015 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (3 pages).
Response to Advisory Action filed on May 14, 2015 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (6 pages).
Notice of Allowance dated Jun. 26, 2015 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (7 pages).
Issue Notification dated Sep. 29, 2015 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (1 pages).
Preliminary Amendment filed on May 21, 2015 with the United States Patent and Trademark Office for U.S. Appl. No. 14/718,955, filed May 21, 2015 and published as US 2015/0344965 on Dec. 3, 2015 (Inventor—Luo et al.; Applicant—The Johns Hopkins University) (3 pages).
Restriction Requirement dated Dec. 30, 2016 by the United States Patent and Trademark Office for U.S. Appl. No. 14/718,955, filed May 21, 2015 and published as US 2015/0344965 on Dec. 3, 2015 (Inventor—Luo et al.; Applicant—The Johns Hopkins University) (11 pages).
Response to Restriction Requirement filed on Mar. 30, 2017 with the United States Patent and Trademark Office for U.S. Appl. No. 14/718,955, filed May 21, 2015 and published as US 2015/0344965 on Dec. 3, 2015 (Inventor—Luo et al.; Applicant—The Johns Hopkins University) (13 pages).
Non Final Office Action filed on Jun. 30, 2017 with the United States Patent and Trademark Office for U.S. Appl. No. 14/718,955, filed May 21, 2015 and published as US 2015/0344965 on Dec. 3, 2015 (Inventor—Luo et al.; Applicant—The Johns Hopkins University) (15 pages).
Jenster G et al: "Functional domains of the human androgen receptor", Journal of Steroid Biochemistry and Molecular Biology, Elsevier Science Ltd. vol. 41, No. 3-8,(1992), pp. 671-675.
Communication pursuant to Article 94(3) EPC dated Apr. 19, 2018 by the European Patent Office for EP Application No. 16152616.5, which was filed on Apr. 16, 2009 and published as EP 3062106 on Aug. 31, 2016 (Applicant—The John Hopkins University) (8 pages).
Final Rejection dated Feb. 23, 2018 by the USPTO for U.S. Appl. No. 14/718,955, filed May 21, 2015, and published as US 2015-0344965 A1 on Dec. 3, 2015 (Inventor—Jun Luo; Applicant—The Johns Hopkins University) (16 pages).
Response to Final Rejection dated Apr. 13, 2018 to the USPTO for U.S. Appl. No. 14/718,955, filed May 21, 2015, and published as US 2015-0344965 A1 on Dec. 3, 2015 (Inventor—Jun Luo; Applicant—The Johns Hopkins University) (18 pages).
Non Final Rejection dated Jul. 25, 2019 by the USPTO for U.S. Appl. No. 15/505,882, filed Feb. 22, 2017 and published as US 2017/0275673 A1 on Sep. 28, 2017 (Inventor—Jun Luo) (17 pages).
Final Rejection dated Jun. 27, 2019 by the USPTO for U.S. Appl. No. 14/718,955, filed May 21, 2015 and published as US 2015-0344965 A1 on Dec. 3, 2015 (Inventor—Jun Luo) (10 pages).
Communication pursuant to Article 94(3)EPC dated Aug. 6, 2019 by the European Patent Office for EP Application No. 16152616.5, which was filed on Apr. 16, 2009 and published as EP 3062106 on Aug. 31, 2016 (Applicant—The John Hopkins University) (4 pages).
Response to Final Rejection dated Aug. 7, 2019 to the USPTO for U.S. Appl. No. 14/718,955, filed May 21, 2015 and published as US 2015/0344965 A1 on Dec. 3, 2015 (Inventor—Jun Luo) (7 pages).
Final Rejection dated Sep. 19, 2019 by the USPTO for U.S. Appl. No. 14/718,955, filed May 21, 2015 and published as US 2015/0344965 A1 on Dec. 3, 2015 (Inventor—Jun Luo) (8 pages).
Communication pursuant to Article 94(3)EPC dated Jul. 8, 2019 by the European Patent Office for EP Application No. 15796390.1, which was filed on May 19, 2015 and published as EP 3146081 on Mar. 29, 2017 (Applicant—The John Hopkins University) (6 pages).
Final Rejection dated Jan. 6, 2020 by the USPTO for U.S. Appl. No. 15/505,882, filed Feb. 22, 2017 and published as US 2017-0275673 A1 on Sep. 28, 2017 (Inventor—Jun Luo) (19 Pages).
Notice of Reasons for Refusal dated Jun. 3, 2019 by the Japanese Patent Office for JP Application No. 2017-511236, which was filed Aug. 25, 2015 and published as 2017-534248 on Nov. 24, 2017 (Applicant—Unknown) (Original—4 pages//Translation—3 pages).
Androgen receptor splice variant-7 predicts resistance to enzalutamide in patients with castration-resistant prostate cancer, Proceedings: AACR Annual Meeting 2014, Apr. 5-9, 2014, (Abstract No. 2910).
EP Communication dated Feb. 21, 2020 by the European Patent Office for EP Application No. 15835018.1, filed Aug. 25, 2015 and published as EP 3186393 A1 on Jul. 5, 2017 (Applicant- The John Hopkins University) (8 pages).

\* cited by examiner

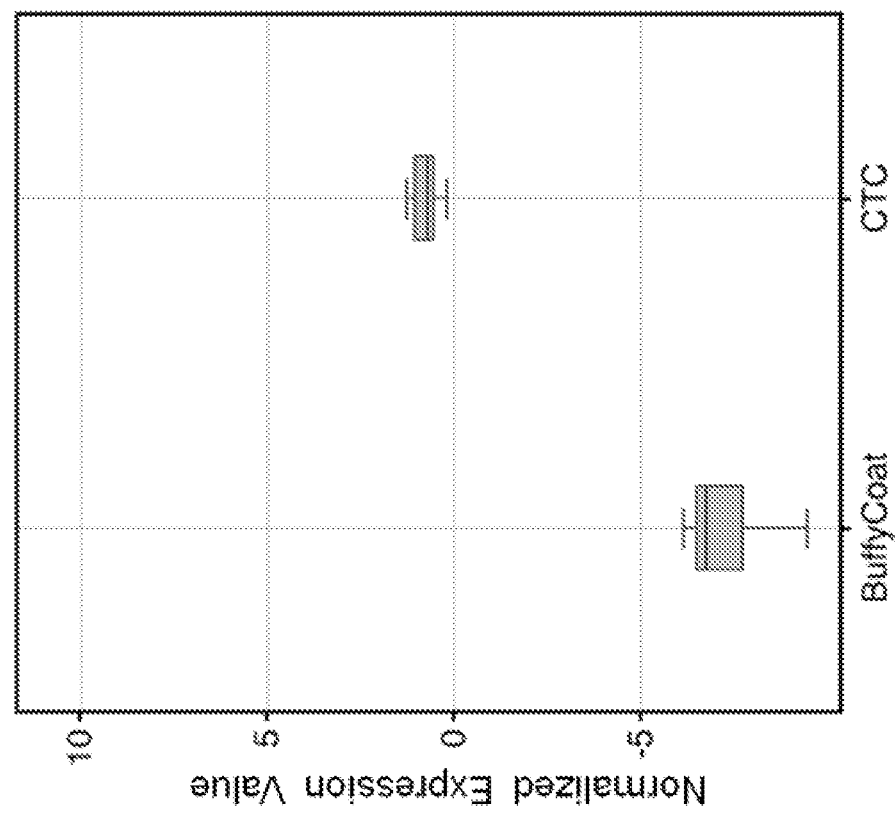
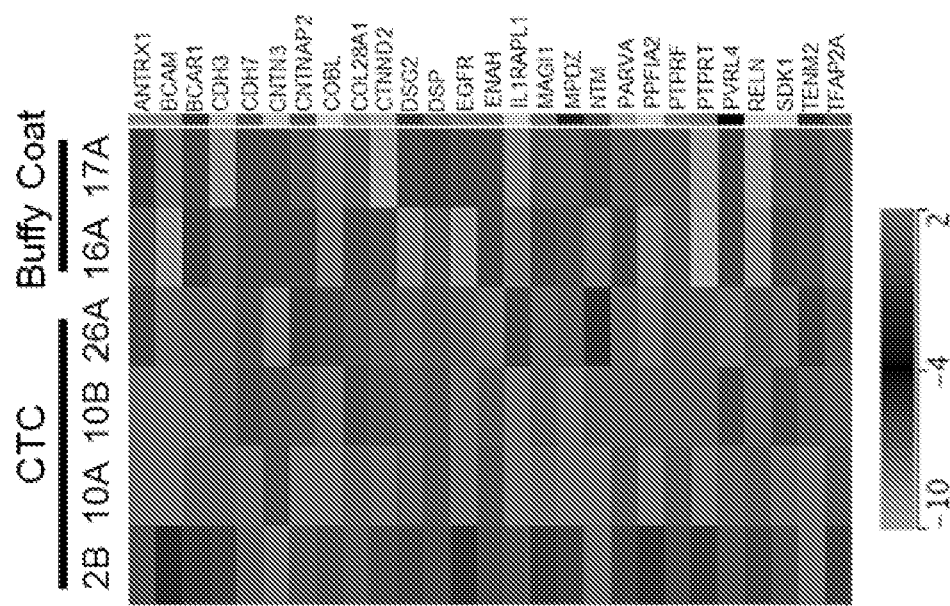
FIG. 4B
FIG. 4A

METHODS FOR IDENTIFYING ANDROGEN RECEPTOR SPLICE VARIANTS IN SUBJECTS HAVING CASTRATION RESISTANT PROSTATE CANCER

This application claims the benefit of and priority under 35 U.S.C. § 371 to PCT/US2015/031584, filed May 19, 2015, which claims the benefit under 35 U.S.C. § 119(e) to U.S. Provisional Patent Application Ser. No. 62/000,263, filed May 19, 2014, which are herein incorporated by reference in their entireties.

REFERENCE TO THE SEQUENCE LISTING

The Sequence Listing submitted Nov. 9, 2016 as a text file named "36406.0010U2_Sequence_Listing.TXT," created on Nov. 9, 2016, and having a size of 1,128 bytes is hereby incorporated by reference pursuant to 37 C.F.R. § 1.52(e)(5).

BACKGROUND OF THE INVENTION

The transcriptome is the complete set of transcripts in a cell, and their quantity, for a specific developmental stage or physiological condition. Understanding the transcriptome is essential for interpreting the functional elements of the genome and revealing the molecular constituents of cells and tissues, and also for understanding development and disease. The key aims of transcriptomics are: to catalogue all species of transcript, including mRNAs, non-coding RNAs and small RNAs; to determine the transcriptional structure of genes, in terms of their start sites, 5' and 3' ends, splicing patterns and other post-transcriptional modifications; and to quantify the changing expression levels of each transcript during development and under different conditions.

Recently, the development of novel high-throughput DNA sequencing methods has provided a new method for both mapping and quantifying transcriptomes. This method, termed RNA-Seq (RNA sequencing), has clear advantages over existing approaches and is expected to revolutionize the manner in which eukaryotic transcriptomes are analysed. It has already been applied to *Saccharomyces cerevisiae, Schizosaccharomyces pombe, Arabidopsis thaliana*, mouse and human cells.

Prostate cancer is the most commonly diagnosed malignancy among men in the USA, and is the second most common cause of cancer mortality in that group. It is estimated that one in six American men will receive a diagnosis of prostate cancer at some point in their lives, at an average age of 68 years. In 2010, there were 217,730 newly diagnosed cases and 32,050 deaths from prostate cancer in the USA alone.

The management of advanced and metastatic disease, however, is more difficult and requires systemic treatment with either hormonal (i.e., androgen deprivation) therapy (ADT) or chemotherapy. Since androgens are the main regulators of prostate cancer growth, the rationale for ADT is that tumor cells deprived of key hormonal growth regulators will either undergo apoptosis or survive in an arrested state in the G1 phase of the cell cycle. The median duration of response to ADT is approximately 18-24 months, after which most patients progress to a more aggressive form of disease termed castration (hormone)-resistant prostate cancer (CRPC).

The outlook for patients with CRPC is quite grim. Several investigators have reported that, without treatment, median survival time ranges from 9.1 to 21.7 months. CRPC is now the second most common cause of male cancer-related mortality. However, recent discoveries pertaining to the biology and pathophysiology of the disease over the last two decades have enabled the development of new therapeutic modalities with the hope of improving those statistics. In recent years, a select few chemotherapy, hormonal, immunotherapy and palliative agents have gained US FDA approval for use in patients with CRPC. Additionally, many experimental anticancer drugs are in development, and there are numerous ongoing clinical trials seeking to elucidate optimal treatment regimens using existing modalities that maximize survival time while minimizing side effects.

Genetic profiling of circulating tumor cells (CTCs) in subjects with CRPC would greatly help diagnosis and identify specific treatment regimens for the subjects. The genomic profile of CTCs from prostate cancer (PCa) are poorly identified due to the rarity of CTCs and the challenge in isolating them.

SUMMARY

The present disclosure provides a method for identifying CTCs from a subject having PCa and using RNA-seq methods, identifying androgen receptor (AR) mutations and CRPC AR splice variants (AR-Vs) from a small sample of blood from the subject.

The present disclosure provides a method for identifying AR mutations and AR-Vs in a sample from a subject comprising: a) obtaining a biological sample from the subject; b) isolating CTCs from the sample in the subject specific for prostate cancer; c) extracting the RNA from the CTCs of b); d) creating a cDNA library from the RNA of c) using 100 bp paired end RNA-seq methodology; e) performing an exonic read of the cDNA library of d) using high throughput sequencing; f) comparing the cDNA corresponding to the AR from the cDNA from the subjects to the control samples; and g) identifying the subjects as having AR mutations and/or AR-Vs (androgen receptor variants, such as AR-V1-9) when the subject samples contain AR mutations and/or AR-Vs and the control samples do not.

BRIEF DESCRIPTION OF THE DRAWINGS

FIG. 3A is a heat map showing unsupervised clustering analysis based on the genome-wide expression profile extracted from the RNA-seq data for CTC samples and buffy coat samples. The buffy coat sample (control) and the CTC samples displayed distinct expression profiles. FIG. 3B is a scatterplot diagram of the same expressed genes identified by RNAseq in CTC and buffy coat cells. FIG. 3C shows the top 1209 differentially expressed genes between CTC and buffy coat cells, and FIG. 3D is a scatterplot of the same genes.

FIGS. 4A-D shows enriched gene ontology categories expressed in CTC and buffy coat cells. FIG. 4A shows genes of cell adhesion, and FIG. 3B shows normalized expression values for buffy coat cells and CTC. FIG. 4C shows genes related to neuron differentiation in CTC and buffy coat cells, and FIG. 4D shows normalized expression values from CTC and buffy coat cells. is a heat map showing a subset of genes identified by high correlation to the androgen receptor (r>0.8). Note that many canonical AR related genes differentiate CTC and leucocytes.

DETAILED DESCRIPTION

Figure 1:
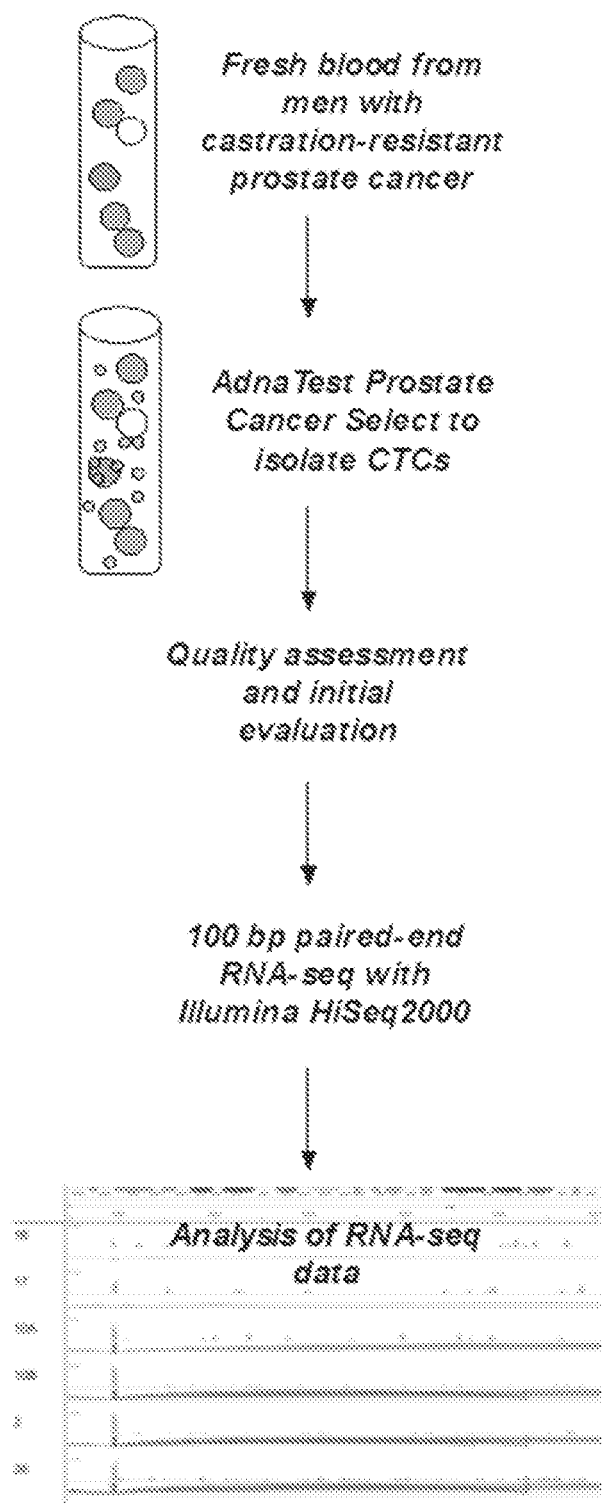
FIG. 1 is a schematic representation of an embodiment of the methods of the present disclosure.

Androgen deprivation therapy (ADT) for advanced prostate cancer is designed to disrupt the androgen receptor (AR) pathway. The intended therapeutic target is the full-length androgen receptor (AR-FL), complete with an intact ligand-binding domain (LBD). Prostate tumors that progress despite first-line ADT (e.g., LHRH analogues), generally termed castration-resistant prostate cancer (CRPC), frequently show continued androgen receptor signaling driven by intratumoral androgens as well as elevated levels of AR-FL. In support of the importance of ligand-driven AR-FL signaling in CRPCs, a number of clinically effective endocrine therapies targeting AR-LBD were recently developed to treat patients with CRPCs (e.g., abiraterone, MDV3100). Nevertheless, the majority of patients progress shortly after treatment, again with reactivated androgen receptor signaling.

In accordance with an embodiment, the present disclosure provides a method for identifying AR mutations and AR-Vs in a sample from a subject comprising: a) obtaining a biological sample from the subject; b) isolating CTCs from the sample in the subject specific for prostate cancer; c) extracting the RNA from the CTCs of b); d) creating a cDNA library from the RNA of c) using 100 bp paired end RNA-seq methodology; e) performing an exonic read of the cDNA library of d) using high throughput sequencing; f) comparing the cDNA corresponding to the AR from the cDNA from the subjects to the control samples; and g) identifying the subjects as having AR mutations and/or AR-Vs when the subject samples contain AR mutations and/or AR-Vs and the control samples do not. Examples of AR variants and mutations as known, as disclosed in U.S. patent application Ser. No. 12/988,299, herein incorporated in its entirety.

AR-Vs are alternatively-spliced transcriptional variants of the AR that encode a truncated AR protein lacking the C-terminal ligand-binding domain but retaining the transactivating N-terminal domain (Dehm, S. M., et al. (2008) Cancer Research 68, 5469-5477; Hu, R., et al. (2009) Cancer Res 69, 16-22). Although these AR-Vs are unable to bind ligand, they are constitutively-active and capable of promoting activation of target genes.

The methods for performing RNA-seq are known and complete descriptions of the general methods can be found in Wang, Z., M. Gerstein, and M. Snyder, RNA-Seq: a revolutionary tool for transcriptomics. Nat Rev Genet, 2009. 10(1): p. 57-63, and Mortazavi, A., et al., Mapping and quantifying mammalian transcriptomes by RNA-Seq. Nature Methods, 2008. 5(7): p. 621-628.

The methods for separation of CTCs from a biological sample in the present disclosure used commercially available magnetic bead separation technology with antibodies specific for prostate cancer tumor cells, such as can be found in AdnaTest Prostate Cancer select procedure (TATAA Biocenter AB, Goteborg, Sweden), for example.

As used herein, the term "treat," as well as words stemming therefrom, includes preventative as well as disorder remitative treatment. The terms "reduce." "suppress," "prevent," and "inhibit," as well as words stemming therefrom, have their commonly understood meaning of lessening or decreasing. These words do not necessarily imply 100% or complete treatment, reduction, suppression, or inhibition. Therapies for the treatment of castration-resistant prostate cancer (CRPC), all of which have produced survival improvements, include but are not limited to, surgical treatments, androgen receptor (AR)-directed therapies (abiraterone, enzalutamide, taxane chemotherapies (docetaxel, cabazitaxel) immunotherapies (sipuleucel-T) and bone-targeting radiopharmaceuticals (radium-223). Of these, the most widely used are the AR-targeting therapies and the chemotherapies. However, mechanisms of response and resistance to these therapies remain poorly understood.

Therapeutic agents or chemotherapeutic agents may be used in treating subject identified as having AR mutations or AR-Vs and include, but are not limited to anti-cancer (anti-neoplastic) agents: Antineoplastic: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil 1131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au198; Hydroxyurea; Idarubicin Hydrochloride; Ifosfamide; Ilmofosine; Interferon Alfa-2a; Interferon Alfa-2b; Interferon Alfa-n; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-neoplastic compounds include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; atrsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocannycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance genie inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfmosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Disclosed methods can further comprise treatment with radiosensitizers. Examples of known radiosensitizers include gemcitabine, 5-fluorouracil, pentoxifylline, and vinorelbine.

The majority of chemotherapeutic drugs can be divided in to: alkylating agents, antimetabolites, anthracyclines, plant alkaloids, topoisomerase inhibitors, monoclonal antibodies, and other antitumor agents. All of these drugs affect cell division or DNA synthesis. Some newer agents do not directly interfere with DNA. These include the new tyrosine kinase inhibitor imatinib mesylate, which directly targets a molecular abnormality in certain types of cancer (chronic myelogenous leukemia, gastrointestinal stromal tumors). In addition, some drugs can be used which modulate tumor cell behaviour without directly attacking those cells. Hormone treatments fall into this category of adjuvant therapies.

Chemotherapeutic agents included within the scope of the disclosed methods can be alkylating agents. Alkylating agents are so named because of their ability to add alkyl groups to many electronegative groups under conditions present in cells. Cisplatin and carboplatin, as well as oxaliplatin are alkylating agents. Other agents are mechloethamine, cyclophosphamide, chlorambucil. They work by chemically modifying a cell's DNA.

Chemotherapeutic agents included within the scope of the disclosed methods can be anti-metabolites. Anti-metabolites masquerade as purine (azathioprine, mercaptopurine) or pyrimidine—which become the building blocks of DNA. They prevent these substances becoming incorporated in to DNA during the 'S' phase (of the cell cycle), stopping normal development and division. They also affect RNA synthesis. Due to their efficiency, these drugs are the most widely used cytostatics.

Chemotherapeutic agents included within the scope of the disclosed methods can be plant alkaloids or terpenoids. These alkaloids are derived from plants and block cell division by preventing microtubule function. Microtubules are vital for cell division and without them it cannot occur. The main examples are *vinca* alkaloids and taxanes.

Chemotherapeutic agents included within the scope of the disclosed methods can be *vinca* alkaloid. *Vinca* alkaloids bind to specific sites on tubulin, inhibiting the assembly of tubulin into microtubules (M phase of the cell cycle). They are derived from the Madagascar periwinkle, *Catharanthus roseus* (formerly known as *Vinca rosea*). The *vinca* alkaloids include: Vincristine, Vinblastine, Vinorelbine, Vindesine, and Podophyllotoxin. Podophyllotoxin is a plant-derived compound used to produce two other cytostatic drugs, etoposide and teniposide. They prevent the cell from entering the G1 phase (the start of DNA replication) and the replication of DNA (the S phase). The exact mechanism of its action still has to be elucidated. The substance has been primarily obtained from the American Mayapple (*Podophyllum peltatum*). A rare Himalayan Mayapple (*Podophyllum hexandrum*) contains it in a much greater quantity, but as the plant is endangered, its supply is limited. Studies have been conducted to isolate the genes involved in the substance's production, so that it could be obtained recombinantly.

Chemotherapeutic agents included within the scope of the disclosed methods can be taxanes. The prototype taxane is the natural product paclitaxel, originally known as Taxol and first derived from the bark of the Pacific Yew tree. Docetaxel is a semi-synthetic analogue of paclitaxel. Taxanes enhance stability of microtubules, preventing the separation of chromosomes during anaphase.

Chemotherapeutic agents included within the scope of the disclosed methods include topoisomerase inhibitors. Topoisomerases are essential enzymes that maintain the topology of DNA. Inhibition of type I or type II topoisomerases interferes with both transcription and replication of DNA by upsetting proper DNA supercoiling. Some type I topoisomerase inhibitors include the camptothecins irinotecan and topotecan. Examples of type II inhibitors include amsacrine, etoposide, etoposide phosphate, and teniposide. These are semisynthetic derivatives of epipodophyllotoxins, alkaloids naturally occurring in the root of American Mayapple (*Podophyllum peltatum*).

Chemotherapeutic agents included within the scope of the disclosed methods can be antitumor antibiotics (Antineoplastics).

Chemotherapeutic agents included within the scope of the disclosed methods can be (monoclonal) antibodies. Monoclonal antibodies work by targeting tumor specific antigens, thus enhancing the host's immune response to tumor cells to which the agent attaches itself. Examples are trastuzumab (Herceptin), cetuximab, and rituximab (Rituxan or Mabthera). Bevacizumab is a monoclonal antibody that does not directly attack tumor cells but instead blocks the formation of new tumor vessels.

Hormonal therapy is included within the scope of the disclosed methods, and is contemplated herein as chemotherapy. Several malignancies respond to hormonal therapy. Cancer arising from certain tissues, including the mammary and prostate glands, may be inhibited or stimulated by appropriate changes in hormone balance. Steroids (often dexamethasone) can inhibit tumor growth or the associated edema (tissue swelling), and may cause regression of lymph node malignancies. Prostate cancer is often sensitive to finasteride, an agent that blocks the peripheral conversion of testosterone to dihydrotestosterone. Breast cancer cells often highly express the estrogen and/or progesterone receptor. Inhibiting the production (with aromatase inhibitors) or action (with tamoxifen) of these hormones can often be used as an adjunct to therapy. Gonadotropin-releasing hormone agonists (GnRH), such as goserelin possess a paradoxic negative feedback effect followed by inhibition of the release of FSH (follicle-stimulating hormone) and LH (luteinizing hormone), when given continuously. Some other tumors are also hormone dependent, although the specific mechanism is still unclear.

In general, when referring to treatment, the therapeutic compositions discussed herein may be administered orally, parenterally (e.g., intravenously or subcutaneous administration), by intramuscular injection, by intraperitoneal injection, transdermally, extracorporeally, by intracavity administration, transdermally, or topically or the like, including topical intranasal administration or administration by inhalant. The topical administration can be ophthalmically, vaginally, rectally, or intranasally. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

As used herein, "parenteral administration" of the composition, if used, is generally characterized by injection. Injectables can be prepared in conventional forms, either as liquid solutions or suspensions, solid forms suitable for solution of suspension in liquid prior to injection, or as emulsions. Parenteral administration includes use of a slow release, a time release or a sustained release system such that a constant dosage is maintained.

The term "therapeutically effective" means that the amount of the composition used is of sufficient quantity to ameliorate one or more causes or symptoms of a disease or disorder, such as aberrant cell growth, tumor development, and cancer. Such amelioration only requires a reduction or alteration, not necessarily elimination. Effective dosages and schedules for administering the disclosed compositions may be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter-indications. Dosage can vary, and can be administered in one or more dose administrations daily, for one or several days. Guidance can be found in the literature for appropriate dosages for given classes of pharmaceutical products.

The specific effective amount of a therapeutic for any particular subject or patient will depend upon a variety of factors including the disease or disorder being treated and the severity of the disorder; the identity and activity of the specific composition employed; the age, body weight, general health, sex and diet of the patient; the time of administration; the route of administration; the rate of excretion of the specific composition employed; the duration of the treatment; drugs used in combination or coincidental with the specific composition employed and like factors well known in the medical arts.

For example, it is well within the skill of the art to start doses of a composition at levels lower than those required to achieve the desired therapeutic effect and to gradually increase the dosage until the desired effect is achieved. One can also evaluate the particular aspects of the medical history, signs, symptoms, and objective laboratory tests that are known to be useful in evaluating the status of a subject in need of attention for the treatment of ischemia-reperfusion injury, trauma, drug/toxicant induced injury, neurodegenerative disease, cancer, or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular subject or patient: (1) a subject's physical condition is shown to be improved (e.g., a tumor has partially or fully regressed), (2) the progression of the disease or condition is shown to be stabilized, or slowed, or reversed, or (3) the need for other medications for treating the disease or condition is lessened or obviated, then a particular treatment regimen will be considered efficacious.

The effective amount of a prescribed therapeutic may be given daily, every other day, weekly, monthly, bi-monthly, every other monthly, yearly, or at any other interval that is determined by the physician or provider to be effective. For example, the effective daily dose can be divided into multiple doses for purposes of administration. Consequently, single dose therapeutic can contain such amounts or sub-multiples thereof to make up the daily dose. Disclosed therapeutics can also be administered as part of a combination of anti-tumor or anti-cancer treatments. In an aspect, disclosed compositions can be administered to the subject or patient prior to treatment with an anti-tumor or anti-cancer treatment. In an aspect, disclosed compositions can be administered concurrently with the anti-tumor or anti-cancer treatment. In an aspect, disclosed composition can be administered subsequent to the anti-tumor or anti-cancer treatment. In an aspect, the patient or subject receives both treatments on an alternating or rotating schedule. In an aspect, the subject or patient receives a singular treatment with the disclosed composition. In an aspect, the subject or patient receives at least one treatment with the disclosed composition. In an aspect, the subject or patient receives at least one treatment with the disclosed composition and at least one other anti-tumor or anti-cancer treatment.

The dosage can be adjusted by the individual physician or the subject in the event of any counter-indications. Dosage can vary, and can be administered in one or more dose administrations daily, for one or several days. Guidance can be found in the literature for appropriate dosages for given classes of pharmaceutical products.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

In an embodiment, the nucleic acids of the disclosure are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates. Ceboids, or Simoids (monkeys) or of the order Anthropoids (humans and apes). An especially preferred mammal is the human.

In accordance with one or more embodiments of the present disclosure, it will be understood that the types of cancer diagnosis which may be made, using the methods provided herein, is not necessarily limited. For purposes herein, the cancer can be prostate cancer. As used herein, the term "cancer" is meant any malignant growth or tumor caused by abnormal and uncontrolled cell division that may spread to other parts of the body through the lymphatic system or the blood stream.

The cancer can be a metastatic cancer or a non-metastatic (e.g., localized) cancer. As used herein, the term "metastatic cancer" refers to a cancer in which cells of the cancer have metastasized, e.g., the cancer is characterized by metastasis of a cancer cells. The metastasis can be regional metastasis or distant metastasis, as described herein.

"Identical" or "identity" as used herein in the context of two or more nucleic acids or polypeptide sequences may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

"Substantially complementary" used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

"Substantially identical" used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

A method of identifying a nucleic acid associated with a disease or a pathological condition is also provided. The method comprises measuring a level of the nucleic acid in a sample that is different than the level of a control or a reference standard. In accordance with an embodiment, the nucleic acid is a mRNA and the detection may be performed by contacting the sample with a probe described herein and detecting the amount of hybridization. PCR may be used to amplify nucleic acids in the sample, which may provide higher sensitivity.

The level of the nucleic acid in the sample may also be compared to a control cell (e.g., a normal cell) to determine whether the nucleic acid is differentially expressed (e.g., overexpressed or underexpressed). The ability to identify mRNAs that are differentially expressed in pathological cells compared to a control can provide high-resolution, high-sensitivity datasets which may be used in the areas of diagnostics, prognostics, therapeutics, drug development, pharmacogenetics, biosensor development, and other related areas.

The expression level of a disease-associated nucleic acid or mRNA provides information in a number of ways. For example, a differential expression of a disease-associated nucleic acid compared to a control may be used as a diagnostic that a patient suffers from the disease. Expression levels of a disease-associated nucleic acid may also be used to monitor the treatment and disease state of a patient. Furthermore, expression levels of a disease-associated mRNA may allow the screening of drug candidates for altering a particular expression profile or suppressing an expression profile associated with disease.

In accordance with another embodiment of the present disclosure, it will be understood that the term "biological sample" or "biological fluid" includes, but is not limited to, any quantity of a substance from a living or formerly living patient or mammal. Such substances include, but are not limited to, blood, serum, plasma, urine, cells, organs, tissues, bone, bone marrow, lymph, lymph nodes, synovial tissue, chondrocytes, synovial macrophages, endothelial cells, and skin. In a preferred embodiment, the fluid is blood or serum.

A method of diagnosis is also provided. The method comprises detecting a differential expression level of one or more disease-associated mRNAs in a biological sample. The sample may be derived from a subject, referred to herein as a biological sample. Diagnosis of a disease state in a subject may allow for prognosis and selection of therapeutic strategy. Further, the developmental stage of cells may be classified by determining temporarily expressed disease-associated mRNAs.

Disclosed herein are methods of assessing resistance to a therapeutic agent in a subject diagnosed with prostate cancer comprising the detection of an AR variant or mutation, such as AR-V7, in a bodily fluid of a subject diagnosed with prostate cancer. For example, the presence of AR-V7 indicates resistance to a therapeutic agent or lack of resistance to difference therapeutic agents. The prostate cancer may be castration-resistant prostate cancer and the therapeutic agent may comprise at least one taxane, enzalutamide or abiraterone, or other therapeutic agents known to those of skill in the art. The bodily fluid may be plasma, serum, or peripheral blood, or other bodily fluids. The bodily fluid, for example, plasma, serum or peripheral blood, may comprise circulating tumor cells (CTC). The bodily fluid may be collected at multiple time points, before diagnosis, following diagnosis of prostate cancer or during the course of treatment: at baseline, at a clinical/biochemical response, and at a clinical/radiographic progression. The clinical/biochemical response may comprise measurement of prostate specific antigen and the clinical/radiographic progression may comprise monitoring symptomatic progression, including but not limited to worsening disease-related symptoms, cancer-related complications, radiologic progression, enlargement in sum diameter of soft-tissue target lesions, increase in number of bone lesions, or death. The presence of AR-V7 is determined by detection assays known those skilled in the art, such as protein or peptide detection methods and/or molecular biological detection, including but not limited to RNA-seq, PCR, qRT-PCR, sequencing, Northern, Southern or Western blots, chip arrays, and antibody assays. In certain embodiments, AR-V7 can be detected with primers or labeled probes, which may comprise one or more of SEQ ID NOS: 1-2 (AR-V7 (forward) 5'-CCATCTTGTCGTCTCG-GAAATGTTA-3' SEQ ID NO: 1; AR-V7 (reverse) 5'-TT-GAATGAGGCAAGTCAGC-CTTTCT-3' SEQ ID NO:2). In certain embodiments, the methods further comprise measuring the amount of AR-FL, and comparing the amount of AR-V7 and AR-FL, in such embodiments, detecting or measuring the amount of AR-FL may comprises the use of primers or labeled probes, which may comprise one or more of SEQ ID NOS: 3-4 (AR-FL (forward) 5'-CAGCCTATT-GCGAGAGAGCTG-3' SEQ ID NO:3; AR-FL (reverse) 5'-GAAAGGATCTGGGCACTTGC-3' SEQ ID NO:4).

Disclosed herein are methods for determining a therapeutic regimen for a subject diagnosed with castration-resistant prostate cancer comprising, detecting the presence of AR-V7 in a bodily fluid of a subject diagnosed with prostate cancer, wherein the bodily fluid comprises circulating tumor cells, and wherein the detection of AR-V7 indicates that the patient has prostate cancer that is resistant to treatment by certain therapeutic agents.

Disclosed herein are methods for treating a subject diagnosed with castration-resistant prostate cancer, wherein the subject has been determined to have the presence and/or amount of a variant AR or mutant AR, such as AR-V7, in a bodily fluid, the bodily fluid may comprise circulating tumor cells, and wherein the detection of AR-V7 indicates that the patient has prostate cancer that is resistant to treatment by certain therapeutic agents, and treating the subject with other cancer treatment methods known to those of skill in the art. Detection and/or measurement of AR mutants and/or variants may comprise RNA-seq methods disclosed herein. Such treatments may comprise determining the level of expression or biological activity of an androgen receptor variant or mutant in a patient sample comprising CTC and/or leukocytes wherein an elevation in the level of expression or biological activity relative to the expression or biological activity in a reference indicates that the subject will not respond to androgen therapy; and administering a treatment therapy, including but not limited to, chemotherapy, radiotherapy, immunotherapy or a pharmaceutical composition that alters expression of an androgen receptor variant polypeptide (e.g., AR-V7) to the subject identified as having said elevation. Therapeutic agents may comprise one or more taxanes, enzalutamide or abiraterone, or other chemotherapeutic agents known (therapeutic agents). Disclosed herein are methods for treating a subject diagnosed with castration-resistant prostate cancer having AR-V7 in a bodily fluid, such as CTC and/or leukocytes, of the subject, wherein the bodily fluid comprises circulating tumor cells, and wherein the detection of AR-V7, such as by RNAseq methods, indicates that the patient has prostate cancer that is either not resistant to treatment by certain therapeutic agents, e.g., a taxane, or is resistant to certain therapeutic agents, e.g., enzalutamide and/or abiraterone, and treating the subject with a treatment therapy, including but not limited to, chemotherapy, radiotherapy, immunotherapy or a pharmaceutical composition/therapeutic agent. The bodily fluid may be collected at multiple time points following diagnosis of prostate cancer or during the course of treatment: at baseline, at a clinical/biochemical response, and at a clinical/radiographic progression. The clinical/biochemical response may comprise measurement of prostate specific antigen and the clinical/radiographic progression may comprise monitoring symptomatic progression, including but not limited to worsening disease-related symptoms, cancer-related complications, radiologic progression, enlargement in sum diameter of soft-tissue target lesions, increase in number of bone lesions, or death. The presence of AR mutants or variants, such as AR-V7 is measured by detection assays known those skilled in the art, including but not limited to, RNAseq methods, which are known to those of skill in the art. In certain embodiments, labeled probes may be used to detect AR-V7 such as one or more of SEQ ID NOS: 1-2. In certain embodiments, the methods further comprise measuring the amount of AR-FL, and comparing the amount of a mutant or variant AR, such as AR-V7, and AR-FL, in such embodiments, measuring the amount of AR-FL may comprises the use of primers or labeled probes, wherein the primers may comprise one or more of SEQ ID NOS: 3-4.

Disclosed herein are methods for utilizing the detection of AR mutants and/or variants, such as AR-V7, as a treatment selection marker. For example, disclosed herein are methods for determining a therapeutic regimen for a subject diagnosed with castration-resistant prostate cancer comprising, detecting the presence of an AR variant or mutant, such as AR-V7, in a bodily fluid of a subject diagnosed with prostate cancer, wherein the bodily fluid comprises circulating tumor cells, wherein the detection of AR-V7 results in determining a therapeutic regimen including or not including one or more therapeutic agents. Detection and/or measurement of AR mutants and/or variants may comprise RNA-seq methods disclosed herein. For example, a subject with prostate cancer may be found to resistant to treatment by certain therapeutic agents, wherein the detection of AR-V7, such as by PCR, indicates that the patient is or is not a candidate for a particular therapy. In an aspect, disclosed herein are methods for utilizing the detection of AR-V7 as a treatment selection marker. For example, disclosed herein are methods for determining a therapeutic regimen for a subject diagnosed with castration-resistant prostate cancer comprising, detecting the presence of AR-V7 in a bodily fluid of a subject diagnosed with prostate cancer, wherein the bodily fluid comprises circulating tumor cells, wherein the detection of AR-V7 results in determining that the patient has prostate cancer that is not resistant to treatment by certain therapeutic agents, for example, a taxane, wherein the detection of AR-V7, such as by RNA seq detection methods, indicates that the patient is a candidate for other cancer treatment therapies, including but not limited to, chemotherapy, radiotherapy, immunotherapy or a therapeutic agent or pharmaceutical composition that alters expression of an androgen receptor variant or mutant polypeptide or polynucleotide (e.g., AR-V7) in the subject. In certain embodiments, the therapy comprises one or more experimental therapies, or one or more existing therapies, or a combination of experimental and existing therapies.

Disclosed herein are kits that are drawn to reagents that can be used in practicing methods disclosed herein. The kits can include any reagent or combination of reagents discussed herein or that would be understood to be required or beneficial in the practice of the disclosed methods. For example, disclosed is a kit for assessing a drug resistance, comprising a nucleic acid having the sequence of all or a portion of a mutant or variant AR, such as AR-V7. The kit can include instructions for using the reagents described in the methods disclosed herein.

Disclosed herein are methods for detecting the presence of androgen receptor variants or mutants such as AR-V7 in bodily fluid samples from prostate cancer patients wherein the samples comprise circulating tumor cells from patients with castration-resistant prostate cancer, comprising detecting in a sample from a prostate cancer patients AR-V7 using RNA sequencing steps.

Disclosed herein are methods and compositions for determining effectiveness of prostate cancer treatment in a subject by determining the presence of, amount of, or change in, an androgen receptor variant or mutant, such as AR-V7, during or after a course of treatment of the cancer, such as with an anti-cancer therapeutic and/or treatment with enzalutamide and abiraterone. The present disclosure comprises methods and compositions for determining effectiveness of castration-resistant prostate cancer treatment in a subject by determining the presence of, amount of, or change in, an androgen receptor variant or mutant, such as AR-V7, during or after a course of treatment of the cancer, such as with a cancer treatment therapeutic and/or treatment with a taxane.

The present disclosure comprises methods and compositions for determining an AR variant or mutant, such as AR-V7 levels in a cell, in an in vitro or in silico assay, in a subject, in a sample from a subject, or from other sources. A method comprises determining in a sample the AR-V7 levels by use of detection methods such as RNA seq methods (RNA sequencing).

It will be appreciated by those skilled in the art that the disclosed polypeptides and nucleic acids as well as the polypeptide and nucleic acid sequences identified from any subject or patient can be stored, recorded, and manipulated on any medium that can be read and accessed by a computer. The disclosed methods can be performed in silico. As used herein, the words "recorded" and "stored" refer to a process for storing information on a computer medium. A skilled artisan can readily adopt the presently known methods for recording information on a computer readable medium to generate a list of sequences comprising one or more of the nucleic acids of the disclosure. Another aspect of the present disclosure is a computer readable medium having recorded thereon at least 2, 5, 10, 15, 20, 25, 30, 50, 100, 200, 250, 300, 400, 500, 1000, 2000, 3000, 4000, 5000, 10,000, or more polypeptides or nucleic acids of the disclosure or polypeptide sequences or nucleic acid sequences identified from any subject or patient.

Thus, provided herein is a computer system comprising a database including records for an AR variant or mutant, such as AR-V7 and nucleic acids encoding AR-V7. Disclosed herein is a computer system comprising a database including records for polypeptides comprising an AR variant or mutant, such as variants of AR-V7 and nucleic acids comprising the sequences encoding variants of AR-V7. Computer readable medium include magnetically readable media, optically readable media, electronically readable media and magnetic/optical media. For example, the computer readable medium may be a hard disc, a floppy disc, a magnetic tape, CD-ROM, DVD, RAM, or ROM as well as other types of other media known to those skilled in the art.

Aspects of the present disclosure include systems, particularly computer systems which contain the sequence information described herein. As used herein, "a computer system" refers to the hardware components, software components, and data storage components used to store and/or analyze the nucleotide sequences of the present disclosure or other sequences. The computer system preferably includes the computer readable media described above, and a processor for accessing and manipulating the sequence data of the disclosed compositions including, but not limited to, the disclosed polypeptides and nucleic acids.

Preferably, the computer is a general purpose system that comprises a central processing unit (CPU), one or more data storage components for storing data, and one or more data retrieving devices for retrieving the data stored on the data storage components. A skilled artisan can readily appreciate that any one of the currently available computer systems are suitable.

In an aspect, the computer system includes a processor connected to a bus which is connected to a main memory, preferably implemented as RAM, and one or more data storage devices, such as a hard drive and/or other computer readable media having data recorded thereon. In an aspect, the computer system further includes one or more data retrieving devices for reading the data stored on the data storage components. The data retrieving device may represent, for example, a floppy disk drive, a compact disk drive, a magnetic tape drive, a hard disk drive, a CD-ROM drive, a DVD drive, etc. In an aspect, the data storage component is a removable computer readable medium such as a floppy disk, a compact disk, a magnetic tape, etc. containing control logic and/or data recorded thereon. The computer system may advantageously include or be programmed by appropriate software for reading the control logic and/or the data from the data storage component once inserted in the data retrieving device. Software for accessing and processing the nucleotide sequences of the nucleic acids of the disclosure (such as search tools, compare tools, modeling tools, etc.) may reside in main memory during execution.

In an aspect, the computer system comprises a sequence comparer for comparing polypeptide and nucleic acid sequences stored on a computer readable medium to another test sequence stored on a computer readable medium. A "sequence comparer" refers to one or more programs that are implemented on the computer system to compare a nucleotide sequence with other nucleotide sequences and to compare a polypeptide with other polypeptides.

Accordingly, an aspect of the present disclosure is a computer system comprising a processor, a data storage device having stored thereon a polypeptide or nucleic acid of the disclosure, a data storage device having retrievably stored thereon reference polypeptide or nucleotide sequences to be compared with test or sample sequences and a sequence comparer for conducting the comparison. The sequence comparer may indicate a homology level between the sequences compared or identify a difference between two or more sequences. For example, a sample comprising AR-V7, or any fragment thereof can be compared with a test sequence from a subject or patient to determine if the test sequence is the same as the reference sequence.

The terminology used herein is for the purpose of describing particular aspects only and is not intended to be limiting.

As used in the specification and the appended claims, the singular forms "a," "an" and "the" can include plural referents unless the context clearly dictates otherwise. Thus, for example, reference to "a compound" includes mixtures of compounds reference to "a pharmaceutical carrier" includes mixtures of two or more such carriers, and the like.

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. When such a range is expressed, an aspect includes from the one particular value and/or to the other particular value. Similarly, when values are expressed as approximations, by use of the antecedent "about," it will be understood that the particular value forms an aspect. It will be further understood that the endpoints of each of the ranges are significant both in relation to the other endpoint, and independently of the other endpoint.

The word "or" as used herein means any one member of a particular list and also includes any combination of members of that list.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the disclosure can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof "Inhibit," "inhibiting," and "inhibition" mean to diminish or decrease an activity, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100 percent, or any amount of reduction in between as compared to native or control levels. In an aspect, the inhibition or reduction is 10-20, 20-30, 30-40, 40-50, 50-60, 60-70, 70-80, 80-90, or 90-100 percent as compared to native or control levels. In an aspect, the inhibition or reduction is 0-25, 25-50, 50-75, or 75-100 percent as compared to native or control levels.

"Modulate", "modulating" and "modulation" as used herein mean a change in activity or function or number. The change may be an increase or a decrease, an enhancement or an inhibition of the activity, function or number.

"Promote," "promotion," and "promoting" refer to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, in an aspect, the increase or promotion can be a 10, 20, 30, 40, 50, 60, 70, 80, 90, 100 percent, or more, or any amount of promotion in between compared to native or control levels. In an aspect, the increase or promotion is 10-20, 20-30, 30-40, 40-50, 50-60, 60-70, 70-80, 80-90, or 90-100 percent as compared to native or control levels. In an aspect, the increase or promotion is 0-25, 25-50, 50-75, or 75-100 percent, or more, such as 200, 300, 500, or 1000 percent more as compared to native or control levels. In an aspect, the increase or promotion can be greater than 100 percent as compared to native or control levels, such as 100, 150, 200, 250, 300, 350, 400, 450, 500 percent or more as compared to the native or control levels.

As used herein, the term "determining" can refer to measuring or ascertaining a quantity or an amount or a change in activity. For example, determining the amount of a disclosed polypeptide in a sample as used herein can refer to the steps that the skilled person would take to measure or ascertain some quantifiable value of the polypeptide in the sample. The art is familiar with the ways to measure an amount of the disclosed polypeptides and disclosed nucleotides in a sample.

The term "sample" can refer to a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g., a polypeptide or nucleic acid). A sample may also be any body fluid or excretion (for example, but not limited to, blood, urine, stool, saliva, tears, bile) that contains cells or cell components.

The disclosure will be further described with reference to the following examples; however, it is to be understood that the disclosure is not limited to such examples. Rather, in view of the present disclosure that describes the current best mode for practicing the disclosure, many modifications and variations would present themselves to those of skill in the art without departing from the scope and spirit of this disclosure. All changes, modifications, and variations coming within the meaning and range of equivalency of the claims are to be considered within their scope.

EXAMPLES

Example 1

The genomic profile of circulating tumor cells isolated from prostate cancer patients is poorly defined. One of the main challenges is the rarity of the target cells. To address this challenge, the present example focused on men with high disease burden and thus likely to have high number of circulating tumor cells compatible with genomic analysis. The RNA profile of circulating tumor cells was defined and methods for personalized treatment were developed.

Patients with metastatic prostate cancer progressing on existing therapies were enrolled into this study under an IRB approved protocol. Circulating tumor cells were isolated through magnetic beads coated with prostate epithelial and tumor-cell specific antibodies. Five milliliter of blood of fresh blood was used to make a single preparation of RNA. Following quality assessment and initial evaluation, qualified RNA specimens were subjected to 100 bp paired-end RNA-seq. Sequencing data was analyzed using RSEM and SpliceMap.

The androgen receptor signature is the dominant signature in circulating tumor cells. Canonical androgen receptor regulated genes were highly expressed in all CTC specimens when compared with RNA extracted from leucocytes (buffy coat cells). In particular, mutations and splice variants of the androgen receptor were discovered and ascertained using this non-invasive approach. Androgen receptor splice variants were frequently detected. Androgen receptor mutations are generally rare events. When detected, androgen receptor mutations may coexist with splice variants, suggesting that these putative mechanisms of castration resistance were not mutually exclusive.

RNA-seq is a powerful technology compatible with analysis of circulating prostate tumor cells. The initial analysis in men with high disease burden will help to drive the development of non-invasive methods of genomic profiling integral to personalized medicine. Signatures identified in the study may be used to design improved CTC capture and detection methods, and for development of novel CTC-based predictive and prognostic markers in men with metastatic prostate cancer.

Tumor metastasis is responsible for most cancer deaths. Metastatic spread through circulating tumor cells (CTCs) constitutes an essential step in the metastatic cascade leading to establish of lesions distant from the primary site. CTCs detected in peripheral circulation represent tumor cells shed into the blood stream from a tumor, either at the primary site or metastatic sites, and were thought to be viable precursors to new tumor lesions. Due to their origin and dynamics, CTCs may help to explain tumor clonal evolution during disease progression or over the course of different treatments. However, CTCs are often present as rare cells in the background of billions of blood cells. Despite the rarity of CTCs, its compatibility with non-invasive sampling has spurred many technical approaches to isolate and detect CTCs. Number of CTCs detected is considered to be prognostic in many types of carcinomas, including breast, prostate, lung, and colon cancers.

A variety of technologies have been developed to isolate and enumerate CTCs on the basis of their unique physical or biological characteristics. The most widely used method is antibody-based capture of CTCs, in which epithelial cell surface marker (eg. EPCAM) antibodies are linked to magnetic beads or chip microcolumns. The isolated CTCs can be enumerated by immunostaining. In addition to enumeration, the molecular signature of the isolated CTCs can be further interrogated by qRT-PCR, microassay, FISH, aCGH, or next generation sequencing. Molecular read-out of the CTCs is widely expected to play a critical role in "liquid biopsy" approaches to tumor classification, prognosis, therapeutic prediction, pharmacodynamics, and discovery of novel drug targets and therapeutic resistance markers.

In the setting of metastatic prostate cancer, CTC enumeration has been evaluated as a marker for prognosis and therapeutic efficacy. A number of pilot studies have profiled the prostate cancer CTC signature by exome sequencing, by mRNA profiling from a single CTC, or by aCGH to analyze genome-wide copy number alterations. The robustness of genome-wide data from these previous studies may be limited by the rarity of cells analyzed. Earlier research by the inventors focused on the predictive value of candidate transcripts detected in CTC samples collected men with mCRPC undergoing treatment with AR-targeted therapies including enzalutamide and abiraterone. The goal of the present study was to generate high-fidelity RNA data by focusing on CTC samples derived from the study that were predicted to have high CTC numbers. In parallel with RNA-seq on CTC, RNA from leukocyte-rich buffy coat was profiled in patients without detectable CTC. By comparing the CTC RNA signature with the leukocyte signature, the CTC-specific signature inclusive of transcript signature and mutation profiles was defined in the context of men with high prostate tumor burden.

TABLE 1

| Patient Samples | | | |
|---|---|---|---|
| Patient # | Age | Sample Type | Treatment |
| 2B | 64 | CTC | After Enzalutamide |
| 10A | 65 | CTC | Before Enzalutamide |
| 10B | 65 | CTC | After Enzalutamide |
| 26A | 58 | CTC | Before Abiraterone |
| 17A | 68 | Buffy Coat | Before 1$^{st}$ line ADT |
| 16A | 78 | Buffy Coat | Before Abiraterone |

Duplicate CTC samples from four blood draws (Table 1) were taken from men with metastatic prostate cancer starting standard-of-care therapy with AR-targeting therapies (including ADT, enzalutamide, and abiraterone) under an IRB-approved protocol and were tested using RNAseq. Buffy coat cells (primarily leukocytes) from two patients in the same study without CTC detection was also collected. For CTC separation, AdnaTest ProstateCancerSelect Kit was used, as has been described. Briefly, 5 mL anti-coagulated blood was incubated with antibody-bound magnetic beads at room temperature for 30 min. The captured cells were harvested by magnet after blood cells were washed away. CTCs were finally lysed in lysis buffer for use. Approximately 300 µl buffy coat from 5 mL anti-coagulated blood was used for comparison or as control cells in RNA extraction with TRIZOL (Invitrogen) and RNeasy Mini Kit (Qiagen) according to the manufacturer's instruction. Quality of RNA in CTC lysate and buffy coat was analyzed by Bio-Analyzer 2000. Quantification of RNA can be determined by known methods, such as Quant-IT PicoGreen assay kit.

RNAseq and Bioinformatical Analysis

Four CTC lysates and RNA from two buffy coat samples underwent cDNA sequencing library construction using TruSeq RNA Sample Prep Kit (Agilent). After confirming the yield and quality of cDNA library, 100 bp paired-end RNAseq was conducted on the sequencing platform Illumina HiSeq2000. Raw data from RNAseq were primarily aligned to Human Genome Reference 19 (hg19) for identification of splice junctions by Tophat2 via a read-mapping algorithm. Cufflinks and DESeq were used to assemble and quantify transcripts. Quality control was performed using Picard Tools and visualized in IGV. To identify single nucleotide polymorphism (SNPs) for mutation discovery, VarScan and snpEFF softwares were used. To look at gene expression, AvadisNGS was carried out and the raw counts for each gene were normalized as Reads Per Kilobase per Million mapped reads (RPKM) for intra- and inter-sampling comparison.

Real Time RT-PCR for RNAseq Result Confirmation

In duplicate samples, real time RT-PCR was performed to determine the expression levels of KLK3, EPCAM, AR-full length (AR-FL), and AR V7 in CTCs as previously described.

RESULTS AND DISCUSSION

Evaluation of RNA Sequencing Data Quality

Figure 2:
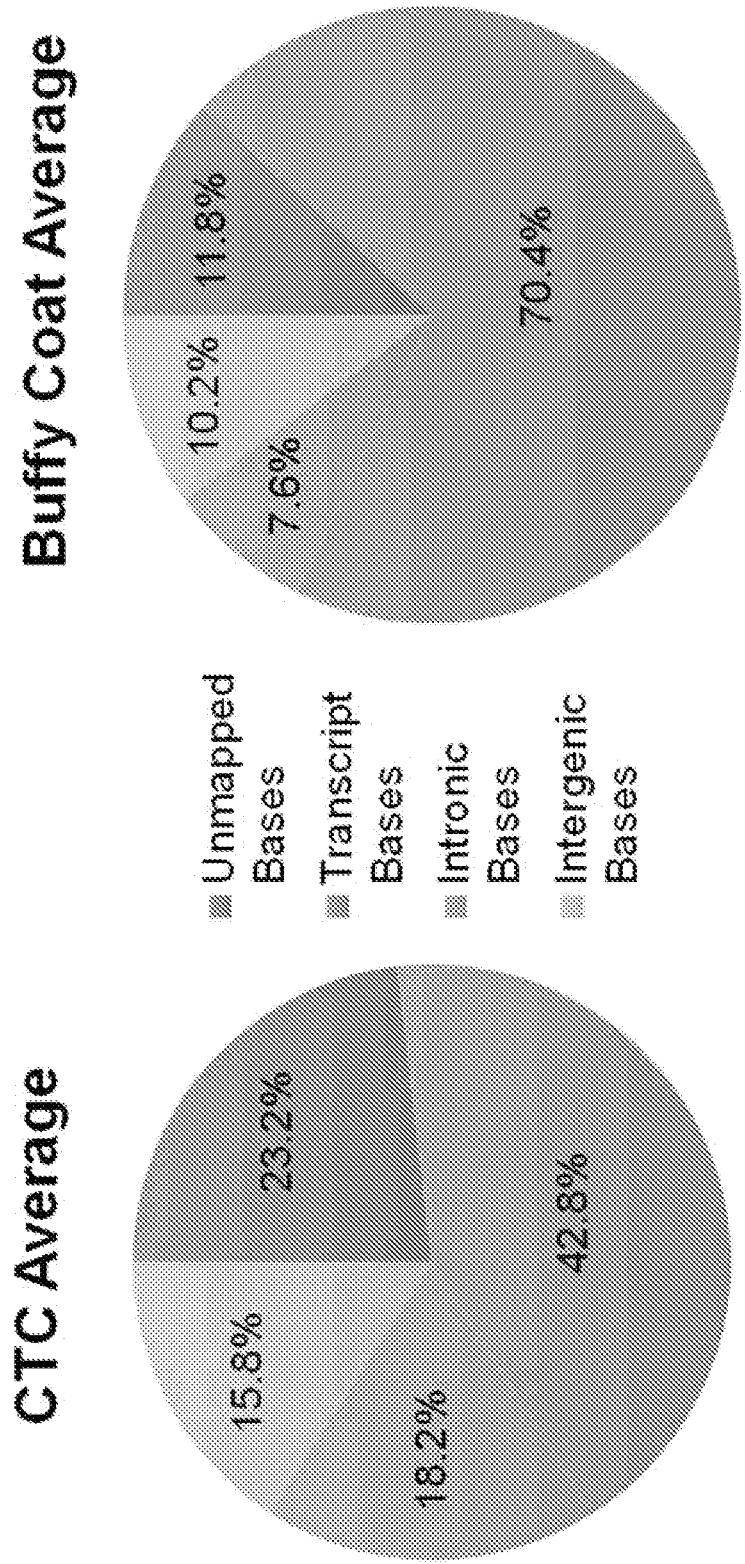
FIG. 2 shows the read distribution in CTC and buffy coat cells in reference to human genome (hg19).
Figure 3B:
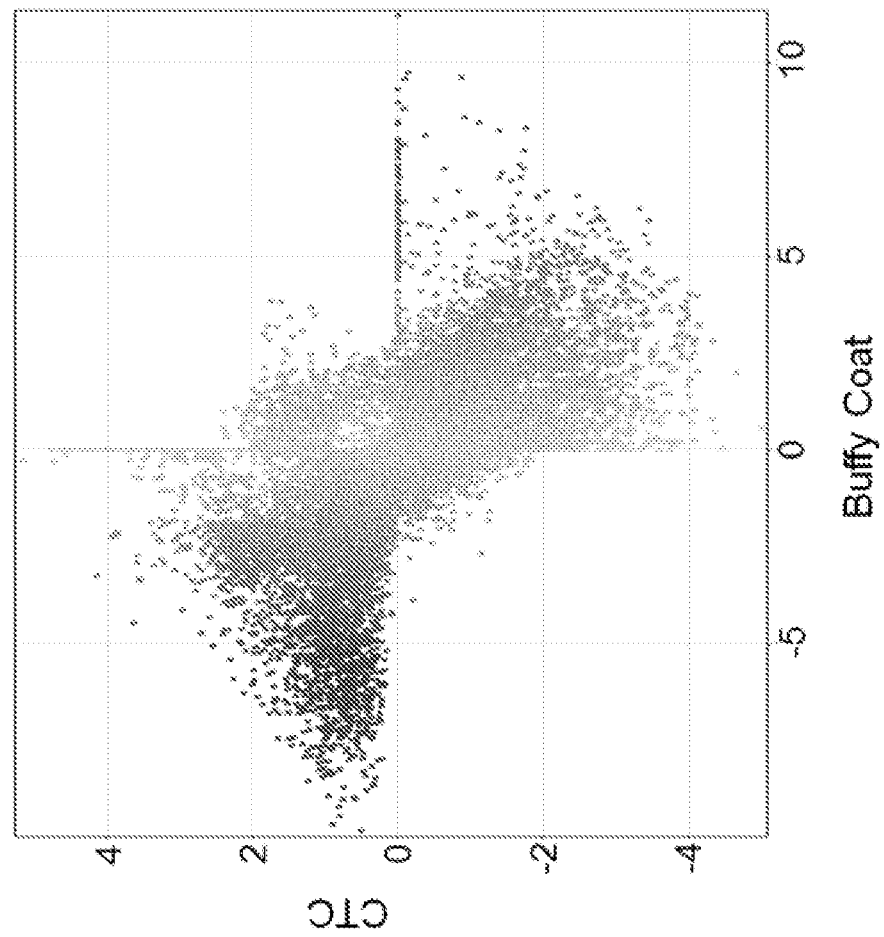
FIGS. 3A-D show comparisons of CTC and buffy coat cells.

A total of 4 CTC samples with high CTC numbers were selected and profiled by RNA-Seq, predicted on the basis of RT-PCR analysis of EPCAM (not shown). In parallel, two buffy coat samples from CTC-negative patients were profiled. All 6 patients were men with mCRPC enrolled in a study evaluating the predictive value of AR-FL/AR-V7 during standard-of-care AR-targeted or Taxane chemotherapies (Table 1). An average 23.7M sequence reads were generated from each sample. The scatterplots of gene quantification results from two replicate runs showed a good correlation, and results from the replicate runs were pooled for further analysis. Sequence reads were mapped to the reference genome (hg19) using TopHat. The pie charts in FIG. 2 show the distribution of reads mapped to exons, introns, and intergenic regions of the genome. For CTC samples, 42.8% reads were mapped to exonic regions, 18.2% to intronic bases, 15.8% to intergenic regions, and 23.2% of the reads were not mapped. Buffy coat samples had more reads aligned to the exons (70.4%), and fewer reads aligning to introns (7.6%) and intergenic regions (10.2%). These results indicate that RNA-seq data from buffy coat samples were of higher quality than those from CTC samples. According to quality control standard which only allows a maximum of 40% unmapped bases/reads, RNA-Seq data quality from all CTC samples were deemed acceptable although the overall lower quality was expected due to rarity of input cell numbers. (See FIGS. 3A and 3B)

Differentially Expressed Genes

Figure 3A:
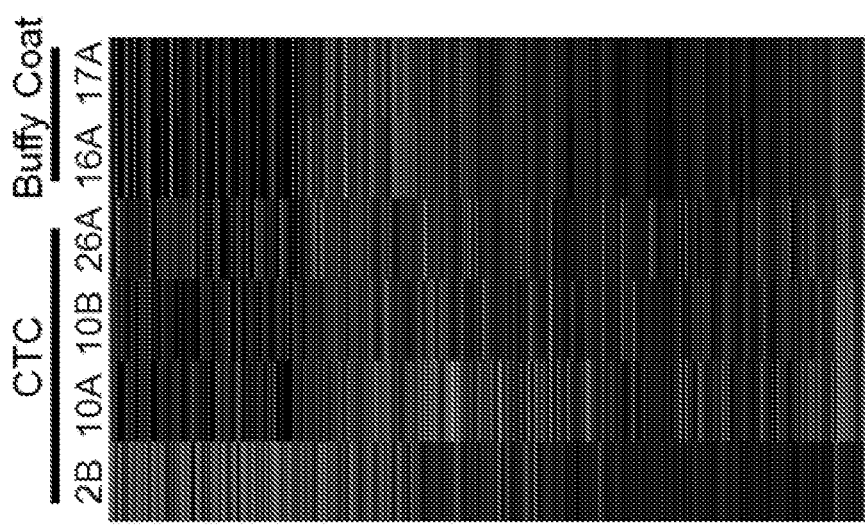
Figure 3D:
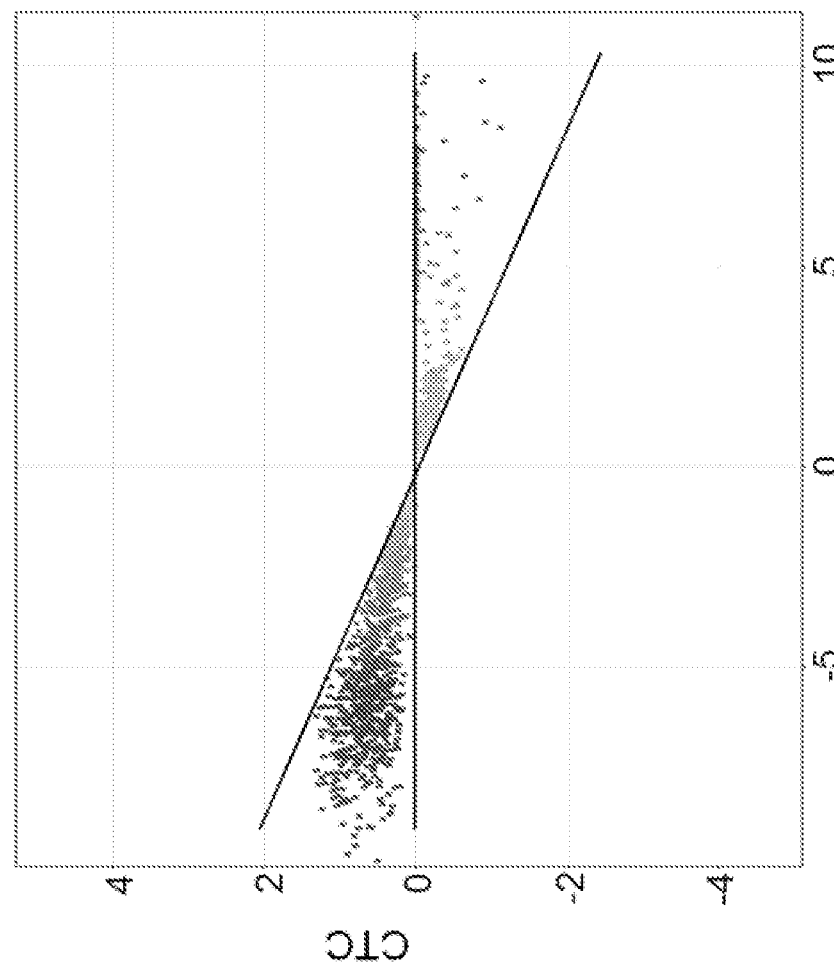
Figure 3C:
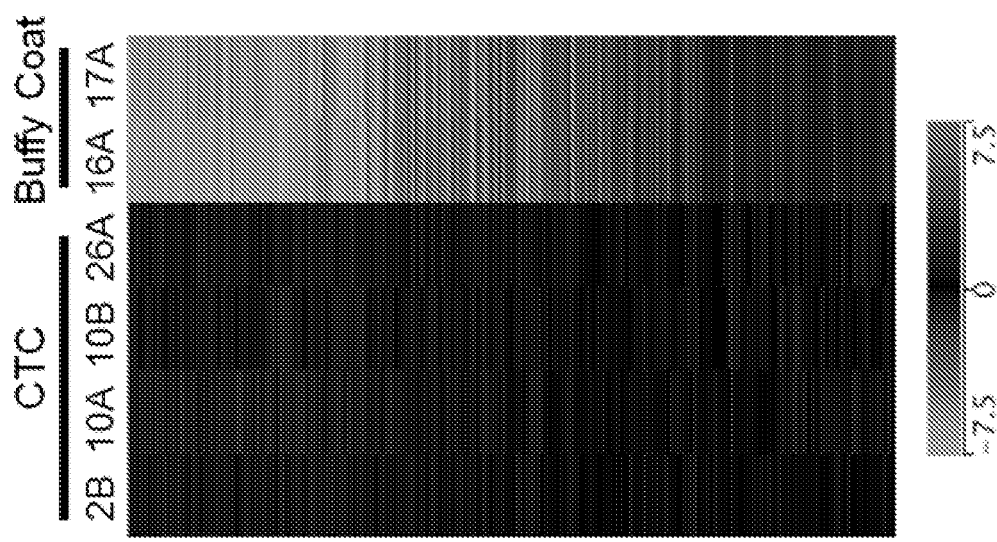
Figure 4D:
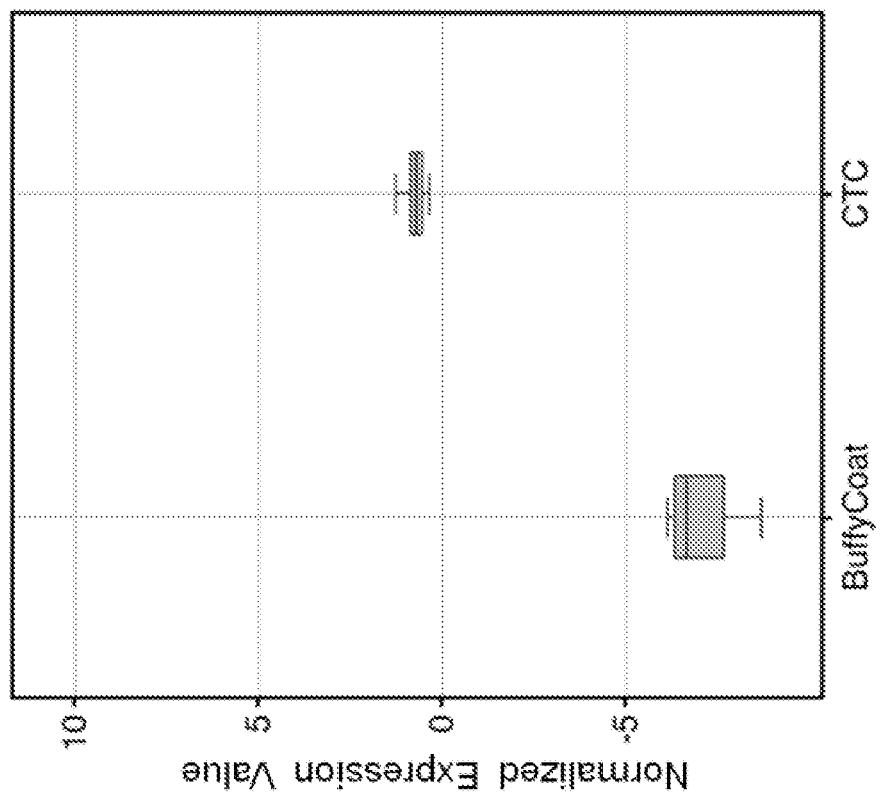
Figure 4C:
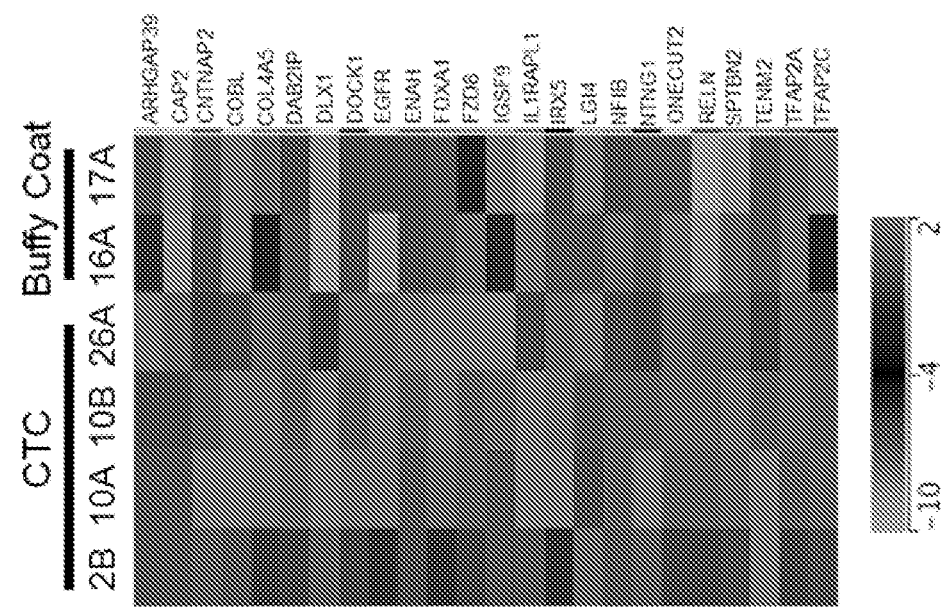

After the transcripts were assembled and quantified by Cufflink, raw counts were normalized as Reads Per Kilobase per Million mapped reads (RPKM) for comparison using DESeq in AvadisNGS. FIG. 3A shows the overall expression pattern of 28308 genes that met the criteria of normalized count above 20. Among 4 CTC samples, sample 2B had a slightly different expression profile from the other three CTC samples (Heat map, FIGS. 3C and 3D). A total of 1209 genes were identified as differentially expressed between CTC and buffy coat samples, using the criteria of a fold change ≥100 and moderated t-test p≤0.05. The differences were mainly driven by those on the second and fourth quadrants. Following enrichment analysis, the most enriched gene ontology category found was the cell adhesion genes (e.g., BCAM) (FIGS. 4A and 4B). These genes show significantly higher expression in CTC than in buffy coat samples, suggesting a potential role of these genes in metastatic spread by facilitating interactions between CTC and the endothelium, platelets, and leukocytes. This group of genes also may provide novel surface marker candidates for CTC selection. Another prominently enriched gene category was the neuron differentiation category (e.g., EGFR, NFIB), also with higher expression in CTC samples (FIGS. 4C and D). These genes may help cancer progression by promoting angiogenesis and neurogenesis. Alternatively, they may be induced by the neuroendocrine differentiation during prostate cancer development.

AR Splicing Variants Detection in CTC

Figure 5:
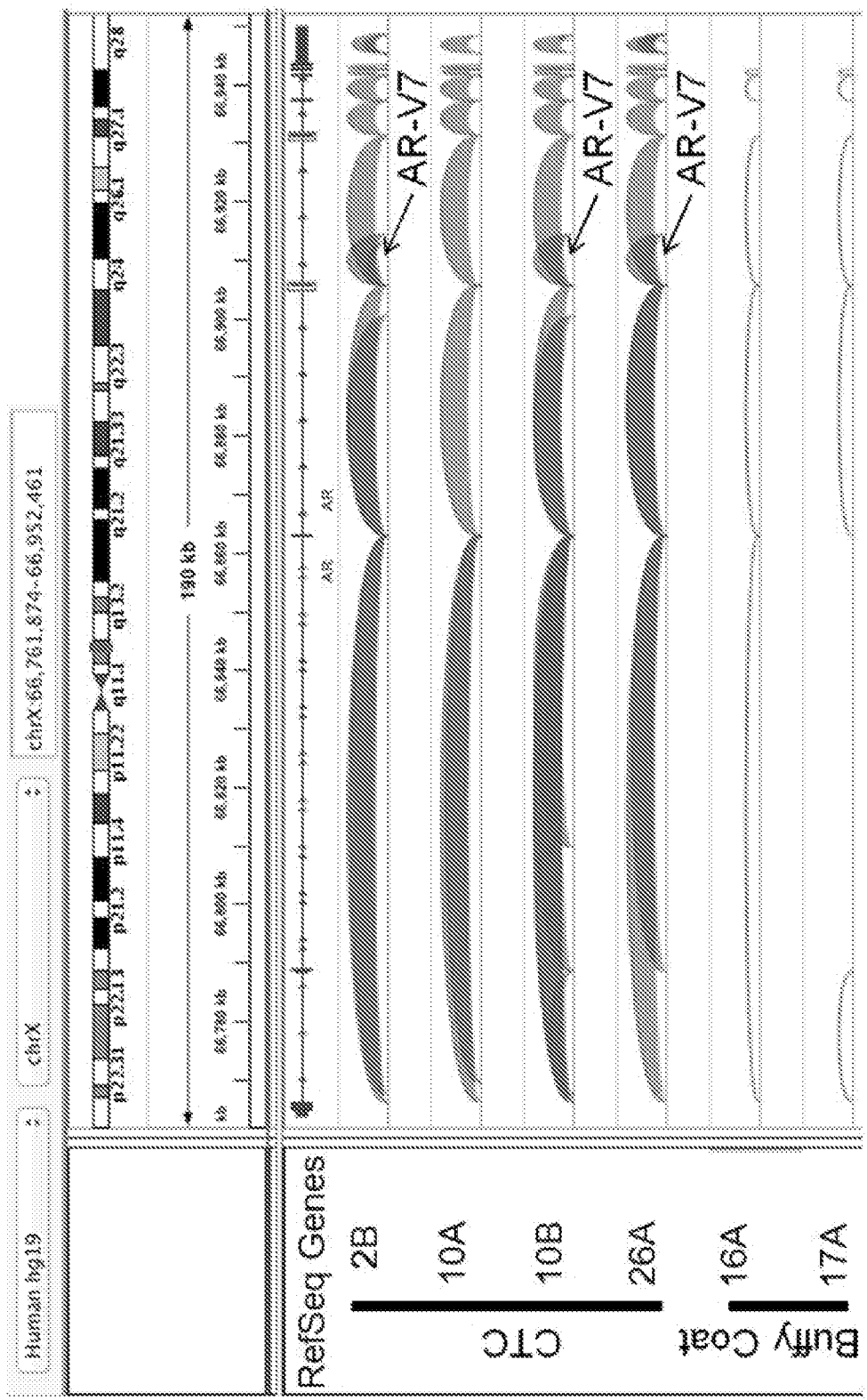
FIG. 5 shows detection of AR splice variants by RNAseq in CTC samples and buffy coat cells. Exonic reads from the cDNA libraries along the AR gene showing AR RNA splice junction tracks depicting sequence reads connecting canonical and cryptic AR exons. The region spanning exon 3 and intron 3 shows positively identified AR-V7 variants.

In addition to transcript quantification, RNA-Seq data also provide information on transcript splicing. We focused on the identification of AR splice variants. Three out of four CTC samples contained dateable AR variants including AR-V7 (FIG. 5). Buffy coat samples had much lower levels of AR-FL expression, and no AR-V7 was detected in these samples. These data further confirms CTC-specific detection of AR transcripts and their utility in detection of the therapy-resistant phenotype.

Mutation Analysis

Figure 6:
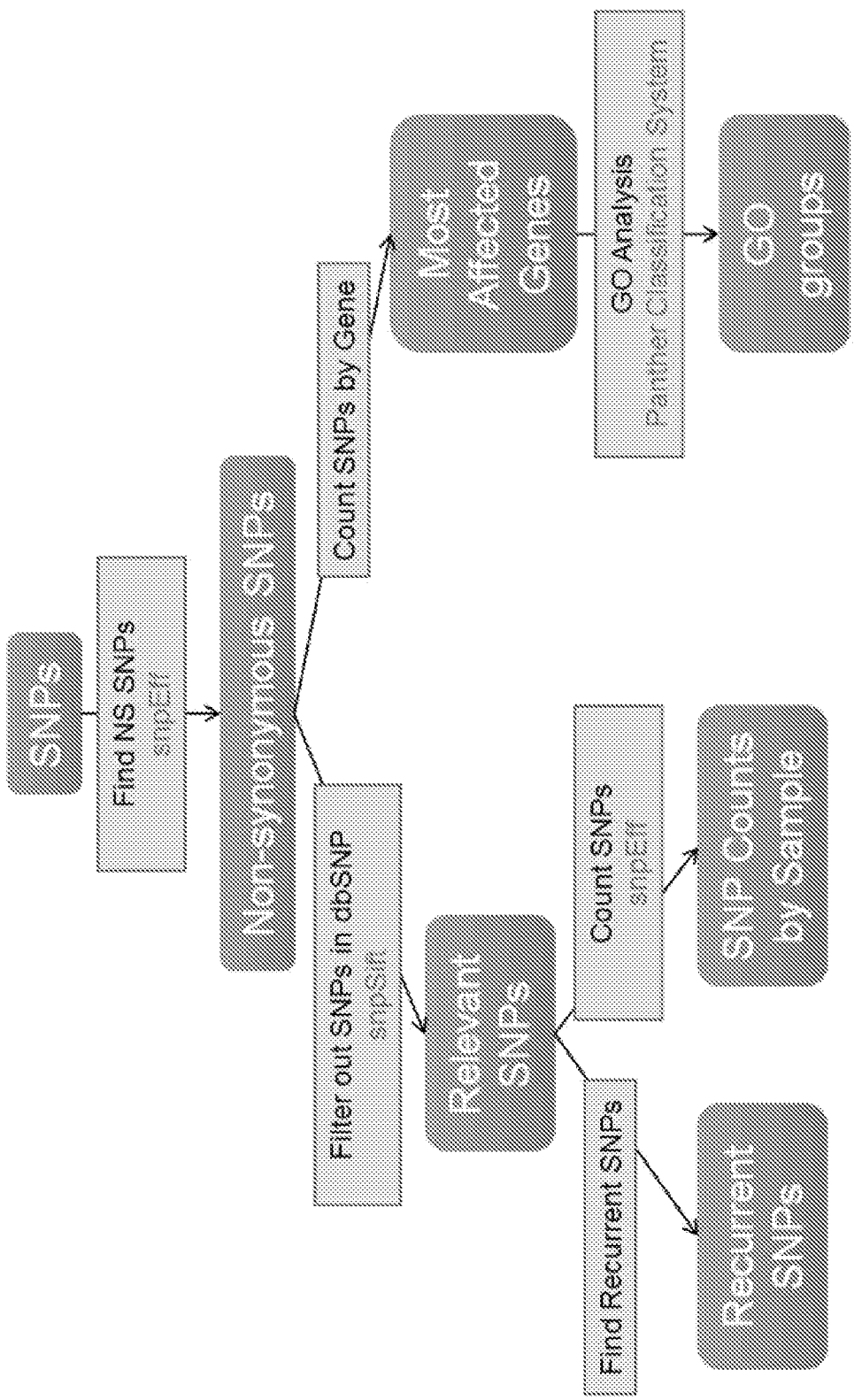
FIG. 6 shows a schematic of methods used in the mutation analysis disclosed herein.
Figure 7:
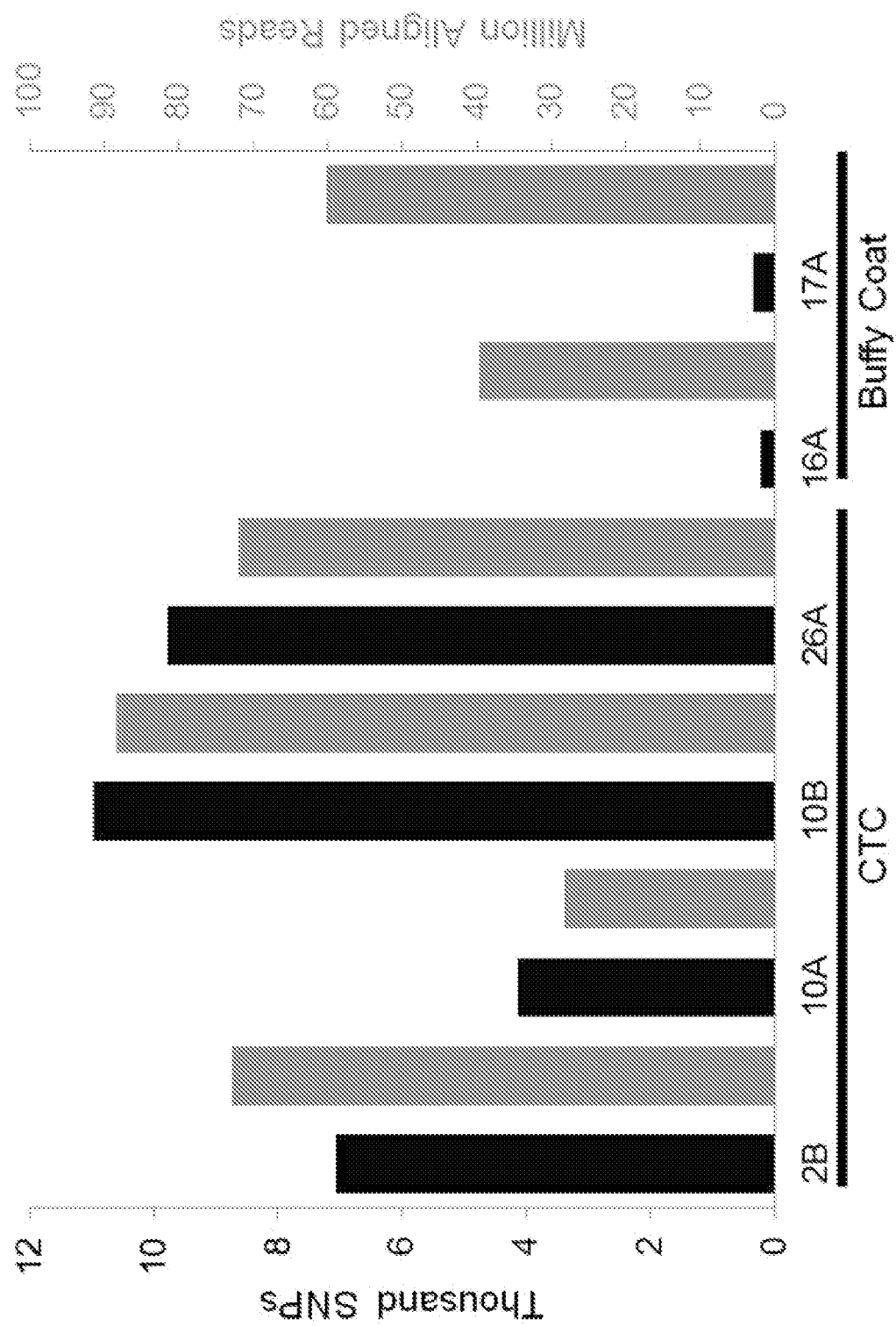
FIG. 7 shows the mutation count from RNAseq data for CTC and buffy coat cells.
Figure 8:
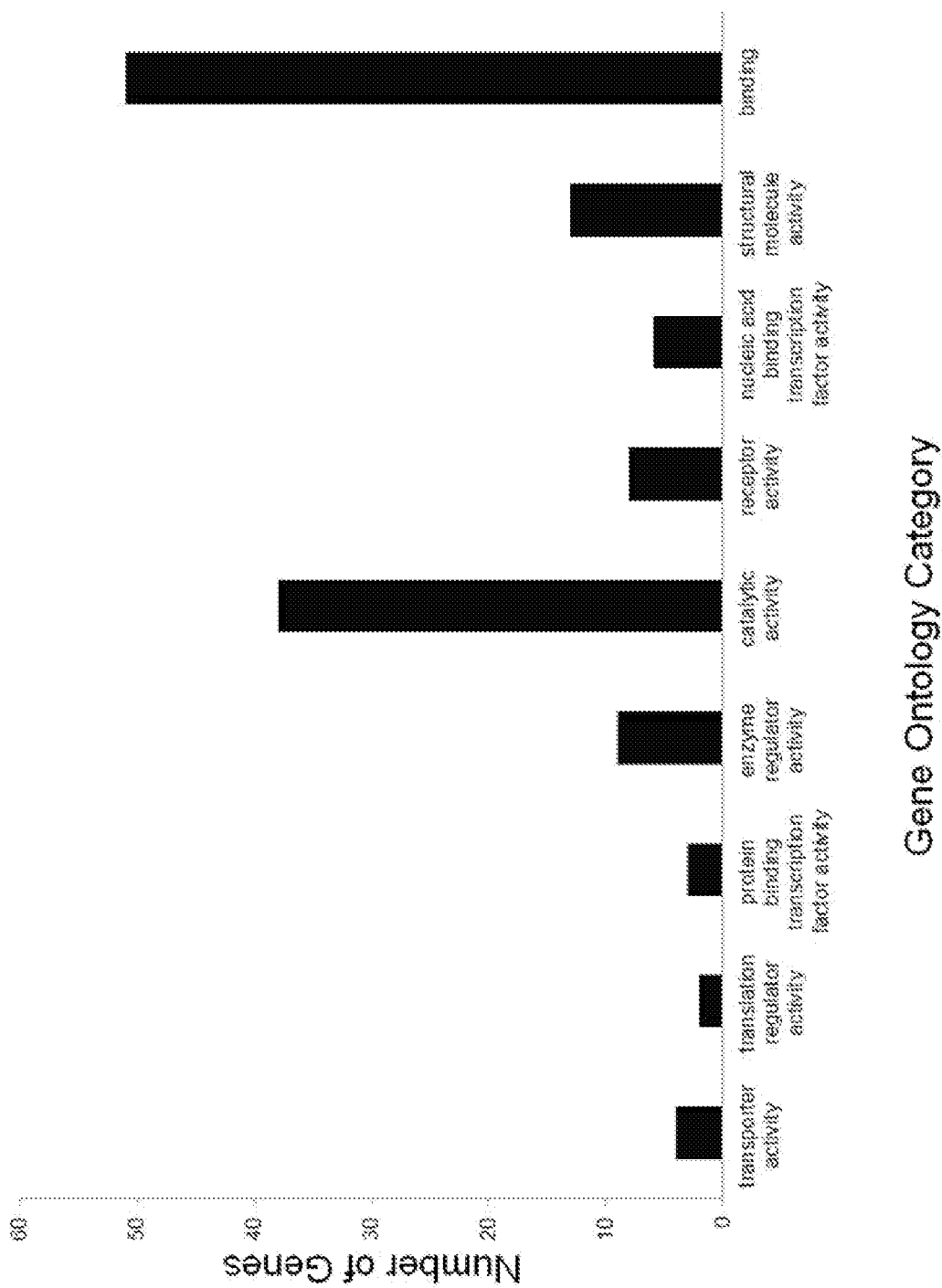
FIG. 8 shows the gene ontology categories that contained mutations found in CTC samples.

Mutations in nucleic acids from CTC samples were found that were not present in the buffy coat samples. First, the SNPs from the aligned reads were annotated by snpEff and non-synonymous coding mutations were culled. SNPs in dbSNP database representing normal variations were removed. The remaining SNPs obtained from dbSNP screening are called "relevant SNPs" (FIG. 6). Using these "relevant SNPs", the recurrent SNPs that occurred in multiple CTC samples were identified and SNP count per sample was calculated (FIG. 6). Results showed that CTC samples had significantly more SNPs/mutations than buffy coat samples (FIG. 7). Next, non-synonymous SNPs were used to count SNPs in each gene and a list of 100 genes with largest number of non-synonymous SNPs for gene ontology analysis (FIG. 8) was compiled. The most affected categories of genes were involved in binding and catalytic activity. These results suggested that mutations can be readily detected in CTC samples, although the biological significance requires further investigation. See Table 2 and Table 3

TABLE 2

| | CTC samples | | | |
|---|---|---|---|---|
| Id Label | 130703 100PE run | 130816 100PE run | Reads as 08282013 | Notes (as 09032013) |
| 2B | 21433430 | 22648192 | 44081622 | Add two 100PE runs data together |
| 10A | 10909877 | 6171361 | 17081238 | Add two 100PE runs data together |
| 10B | 41320901 | 11747769 | 53068670 | Add two 100PE runs data together |
| 26A | 35234261 | 6669372 | 41903633 | Add two 100PE runs data together |

TABLE 3

| | Buffy Coat Samples (Control) | | | |
|---|---|---|---|---|
| Id Label | 130703 100PE run | 130816 100PE run | Reads as 08282013 | Notes (as 09032013) |
| 16A | 13624278 | 5906494 | 19530772 | Add two 100PE runs data together |
| 17A | 13841415 | 17181850 | 31023265 | Add two 100PE runs data together |

Table 4 shows recurrent mutations identified in CTC samples using RNA seq.

TABLE 4

| Position | Gene | Samples | Reference Codon | Variant Codon | Average Variant Frequency |
|---|---|---|---|---|---|
| chr1: 146395447 | NBPF12 | 10A, 10B, 26A | R(AGA) | G(GGA) | 0.6897 |
| chr2: 131414737 | POTEJ | 2B, 10B, 26A | M(ATG) | V(GTG) | 0.4898 |
| chr11: 18422528 | LDHA | 2B, 10A, 26A | N(AAC) | I(ATC) | 0.4304 |
| chr10: 99190854 | PGAM1 | 2B, 10A | H(CAT) | P(CCT) | 1.0000 |
| chr2: 217526577 | IGFB2 | 10A, 10B | C(TGC) | S(TCC) | 1.0000 |

NBPF12 (1q21) = neuroblastoma breakpoint family member 12 -> = COAS1, KIAA1245, associated with neuroblastoma (malignant tumor from nerve tissue, usually in children) (copy number variations)(19536264), amplified in solid tumors - potential oncogene (11948409)
POTEJ (2q21.1) = POTE (primate specific gene family) ankyrin domain family member J -> = POTE2beta, expressed in prostate, expressed in normal and cancerous prostate (12475935), "suggested to act in signaling pathway in the reproductive system), probably b/c of loss of stop codons, encodes chimeric POTE-actin (fusion of POTE and actin) (19463943), predominantly expressed in cancers (along with 2alpha, 2gamma, 22) while more diverse POTE expression in normal tissue (16397215)
LDHA (11p15.4) = lactate dehydrogenase A -> = LDH1, LDHM, GSD11, PIG19, HEL-S-133P, key mediator of aerobic glycolysis (preferential use of glycolysis even though oxygen present to meet cellular metabolic demands) which is present in almost all cancer(23583676), silencing in prostate cancer results in significant sensitization to radiotherapy (24714743), Warburg effect (http://cancerres.aacrjournals.org/content/66/18/8927.long)
PGAM1 (10q25.3) = phosphoglycerate mutase 1 (brain) -> = PGAMA, PGM-B, HEL-S-35, catalyzes 3-PGA to 2-PGA (4811757), when active stabilizes tumours, negative transcriptional target of TP53 (up-regulated in human cancers) (23653202)
IGFBP2 (2q33-q34) = insulin-like growth factor binding protein 2 -> = IBP2, IGF-BP53, concentration up in tumors (24275430, 24069370), high expression associated with chemoresistance in adult acute myeloid leukemia (21899885), plays a role in hyperglycemia-induced chemoresistance of prostate cancer (23959956), castration-induced increases expression and proliferation of tumors in LNCaP (12839944)

Androgen Receptor Signature

Figure 9:
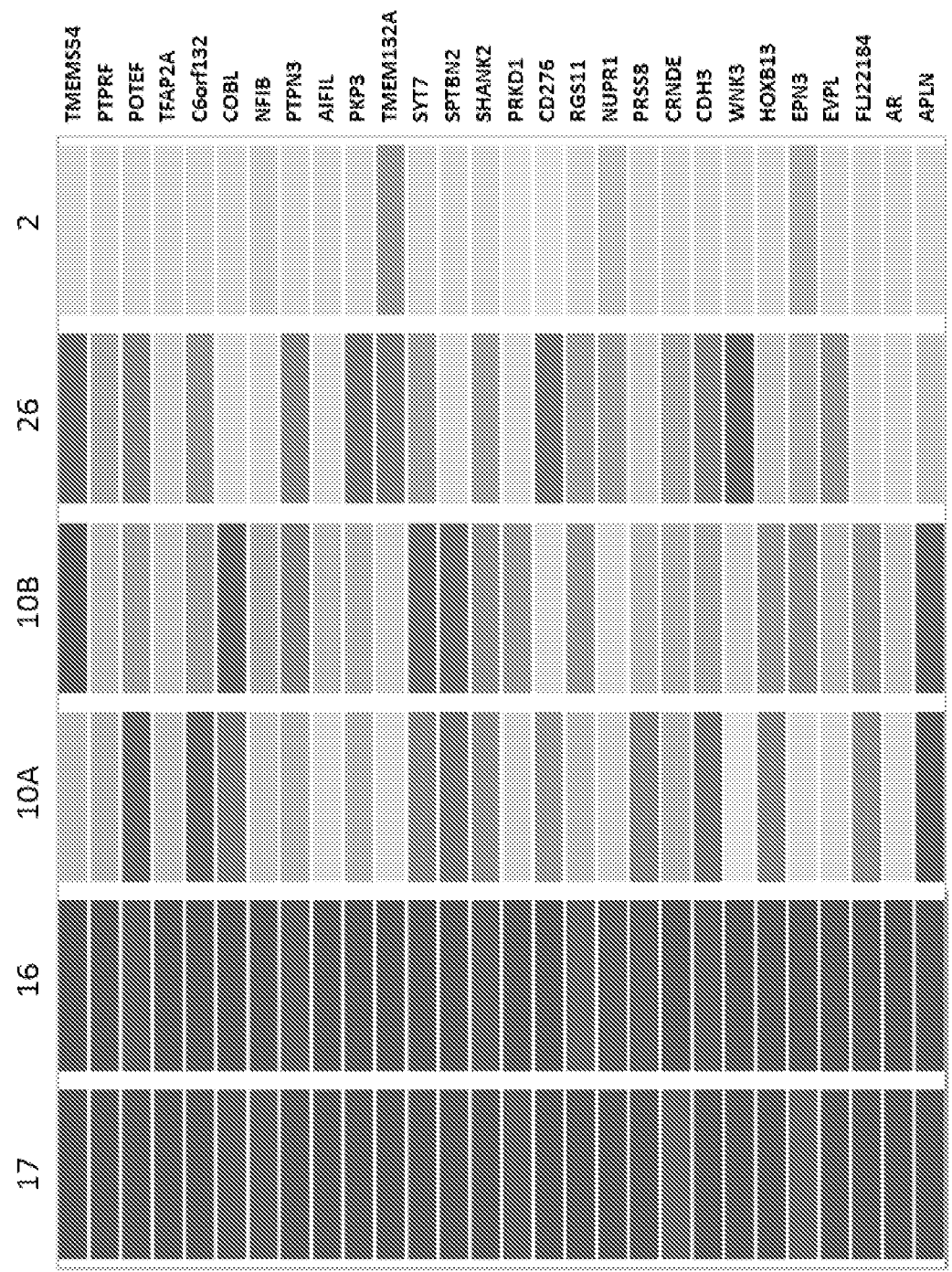
FIG. 9 shows a subset of genes identified by high correlation to the androgen receptor (r>0.8). Many canonical AR related genes differentiate CTC and leucocytes. Columns from left to right are Samples 17, 16, 10A, 10B, 26 and 2B.

Androgen receptor-related gene expression patterns in CTC was also examined. FIG. 9 shows the list of genes correlated with AR expression in the profiled samples. AR-related genes are uniformly overexpressed in CTC samples when compared with buffy coat samples, and represent a dominant signature specific to CTC samples. These AR-regulated genes can serve as non-invasive biomarkers. The present disclosure contemplates methods of detecting the biomarker genes shown in FIG. 4 and FIG. 9 in diagnosis of androgen receptor pathologies. These AR-related genes are expressed in higher amount in CTC, compared to leucocytes, in subjects and thus a comparison of the amount in of expressed genes, for example one or more genes disclosed in FIGS. 4A and 4C and FIG. 9, found in CTC compared to the expression level in leucocytes. A method comprises detecting, from a body sample from a subject, the level of one or more of AR-related genes (FIG. 4 and/or FIG. 9) wherein an increased amount found in CTC indicates that the subject has an AR-related pathology, such as prostate cancer, including castration resistant prostate cancer. These AR-related genes may be used in the methods disclosed and claimed herein, such as choosing treatment regimens, treating and diagnosing subjects, and others disclosed herein.

Simultaneous Detection of AR Transcription of AR Mutation

Figure 10A:
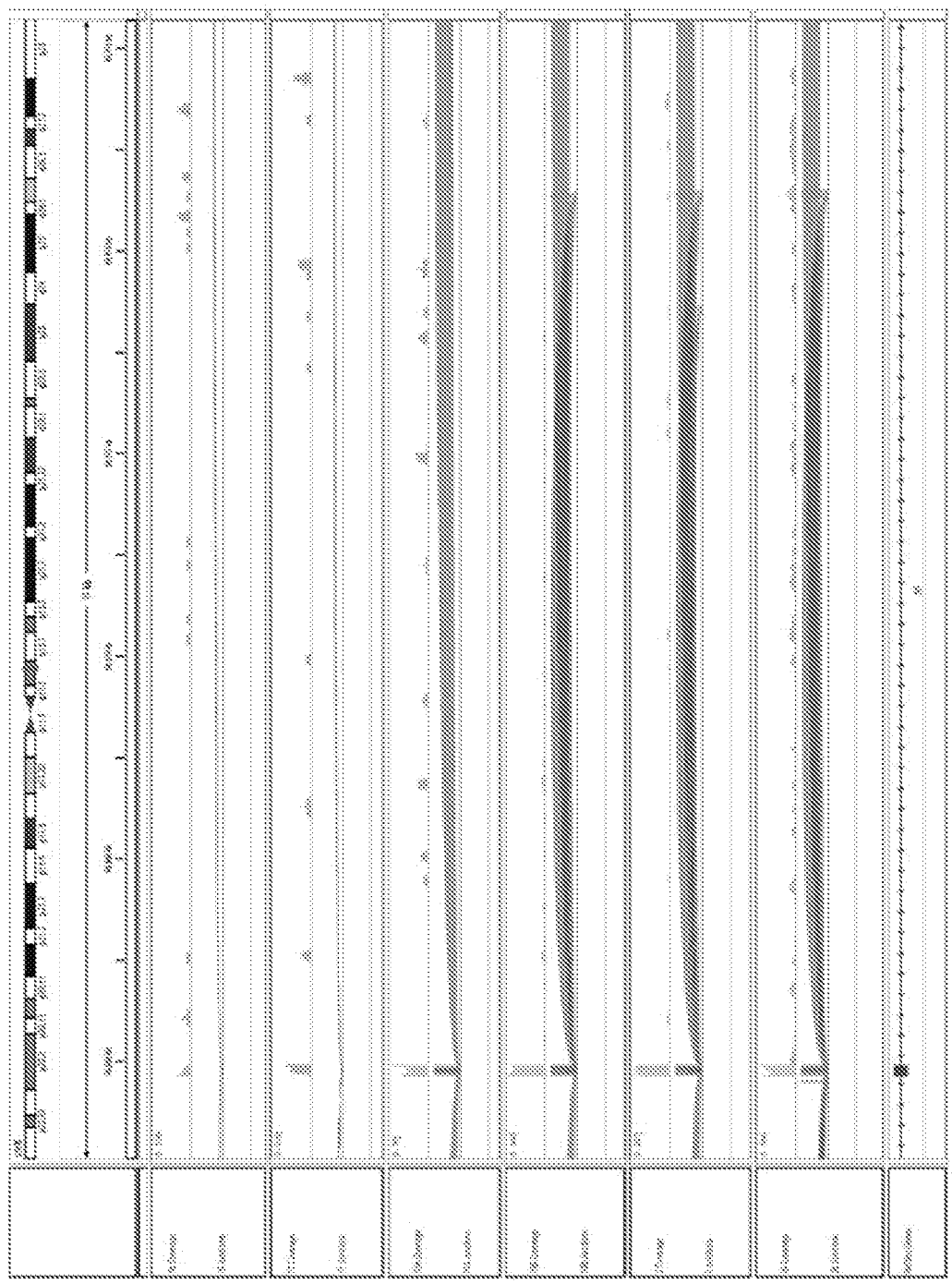
FIG. 10A-B are read coverage showing AR RNA splice junction tracks depicting sequence reads connecting canonical and cryptic AR exons (10A), as well as an AR mutation (L701H) detected in 10A and 10B samples (10B). The enlarged region spanning exon 3 and intron 3 (10A) shows positively identified AR-V7 variants, with numbers in parentheses indicating the number of variant-specific reads over the number of AR-FL-specific reads.
Figure 10B:
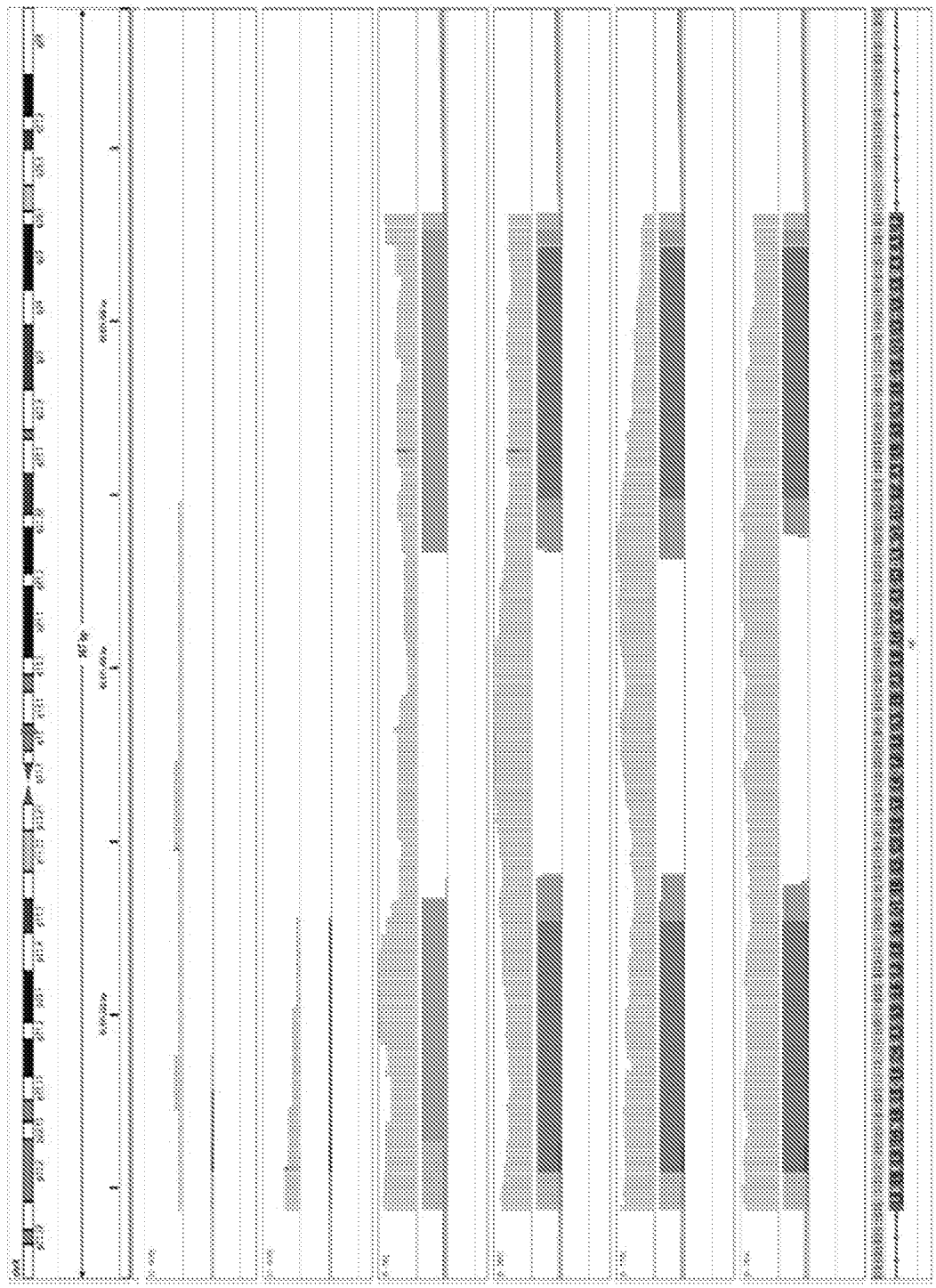

Patient #10 was shown to have the L701H mutation that is known to give rise to glucocorticoid-sensitive AR, such that the AR can be activated upon stimulation with glucocorticoid (FIGS. 10A and 10B). AR mutations are generally rare events. Data from patient #10 suggest gain-of-function AR mutation (L701H) may coexist with AR-V7, suggesting that these mechanisms of castration resistance are not mutually exclusive, and simultaneous detection of mutually exclusive mechanisms of resistance may be possible using non-invasive approaches.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

References

Circulating tumor cells: approaches to isolation and characterization. J Cell Biol. 2011 Feb. 7; 192(3): 373-382 (review).

Circulating tumor cells predict survival benefit from treatment in metastatic castration-resistant prostate cancer. Clin. Cancer Res. 2008. 14:6302-6309

BMC Cancer. 2012; 12: 78. Isolation and genomic analysis of circulating tumor cells from castration resistant metastatic prostate cancer Trapnell C, Pachter L, Salzberg S L. TopHat: discovering splice junctions with RNA-Seq. Bioinformatics. 2009; 25:1105-1111.

Trapnell C, Roberts A, Goff L, et al. Differential gene and transcript expression analysis of RNA-seq experiments with TopHat and Cufflinks. Nat Protoc. 2012; 7:562-578.

Robinson J T, Thorvaldsdottir H, Winckler W, et al. Integrative genomics viewer. Nat Biotechnol. 2011; 29:24-26.

Trapnell, Cole; Williams, Brian A; Pertea, Geo; Mortazavi. Ali; Kwan, Gordon; van Baren, Marijke J; Salzberg, Steven L; Wold, Barbara J; Pachter, Lior (May 2010). "Transcript assembly and quantification by RNA-Seq reveals unannotated transcripts and isoform switching during cell differentiation". Nat Biotechnol 28 (5): 511-515. (Cufflinks)

What is claimed is:

1. A method for identifying androgen receptor-variant 7 (AR-V7) in a sample from a subject comprising:
   a) isolating circulating tumor cells (CTCs) from a biological sample from a subject specific for prostate cancer;
   b) extracting the RNA from the isolated CTCs;
   c) creating a cDNA library from the RNA of b) using 100 bp paired end RNA-seq;
   d) performing an exonic read of the cDNA library of c) using high throughput sequencing;
   e) comparing the cDNA corresponding to the AR from the cDNA from the subject to a control sample; and
   f) identifying the subject as having AR-V7 when the subject's sample contains AR-V7.

2. The method of claim 1, further comprising providing an appropriate therapeutic treatment regimen when the subject is identified as having AR-V7.

3. A method for monitoring a subject undergoing treatment for prostate cancer comprising:
   a) performing the method of claim 1 on a sample from the subject;
   b) administering a selected chemotherapy to the subject;
   c) repeating step a) after a period of time; and d) analyzing the level of AR-V7 before and after b) and making a determination of the existence of a difference in the level of AR-V7 after treatment.

4. A method of assessing resistance to a therapeutic agent in a subject diagnosed with prostate cancer comprising detecting the presence of AR-V7 in a bodily fluid of a subject diagnosed with prostate cancer by the method of claim 1, wherein the presence of AR-V7 indicates resistance to a therapeutic agent.

5. The method of claim 4, wherein the prostate cancer is castration-resistant prostate cancer.

6. The method claim 4, wherein the therapeutic agent is enzalutamide or abiraterone.

7. The method of claim 4, wherein the bodily fluid is collected at multiple time points following diagnosis of prostate cancer or during the course of treatment.

8. The method of claim 7, wherein the bodily fluid is collected at baseline, at a clinical/biochemical response, and at a clinical/radiographic progression.

9. The method of claim 4, further comprising
(a) measuring the amount of full-length androgen receptor (AR-FL), and (b) comparing the amount of AR-V7 and AR-FL.

10. A method of assessing whether a patient having castration-resistant prostate cancer is resistant to a therapeutic agent comprising detecting the presence of AR-V7 in a bodily fluid of a subject diagnosed with prostate cancer using the method of claim 1, wherein the bodily fluid comprises circulating tumor cells, and wherein detection of AR-V7 is an independent factor for indicating resistance to a therapeutic agent.

11. The method claim 10, wherein the therapeutic agent is enzalutamide or abiraterone.

12. The method of claim 10, wherein the bodily fluid from a patient is collected at multiple time points following diagnosis of prostate cancer or during the course of treatment.

13. The method of claim 10, further comprising
(a) measuring the amount of AR-FL, and (b) comparing the amount of AR-V7 and AR-FL.

14. A method for determining a therapeutic regimen for a subject diagnosed with castration-resistant prostate cancer comprising,
a) detecting the presence of AR-V7 in a bodily fluid of a subject diagnosed with prostate cancer using the method of claim 1,
b) wherein the bodily fluid comprises circulating tumor cells,
c) wherein the detection of AR-V7 by PCR results in determining that the patient has prostate cancer that is resistant to treatment by certain therapeutic agents.

15. The method of claim 14, wherein the bodily fluid from a patient is collected at multiple time points following diagnosis of prostate cancer or during the course of treatment with alternative therapies.

16. The method of claim 14, further comprising
(a) measuring the amount of AR-FL, and (b) comparing the amount of AR-V7 and AR-FL.

17. A method for determining a therapeutic regimen for a subject diagnosed with castration-resistant prostate cancer comprising,
a) detecting the presence of AR-V7 in a bodily fluid of a subject diagnosed with prostate cancer using the method of claim 1,
b) wherein the bodily fluid comprises circulating tumor cells,
c) wherein the detection of AR-V7 results in determining that the patient has prostate cancer that is resistant to treatment by certain therapeutic agents, and/or
d) wherein the detection of AR-V7 results in determining that the patient is a candidate for alternative therapy.

18. The method of claim 1, wherein the CTCS are isolated from the biological sample using magnetic beads coated with prostate epithelial and tumor-specific antibodies.

* * * * *

SEQUENCE LISTING

```
<160> NUMBER OF SEQ ID NOS: 4

<210> SEQ ID NO 1
<211> LENGTH: 26
<212> TYPE: DNA
<213> ORGANISM: Artificial sequence
<220> FEATURE:
<223> OTHER INFORMATION: Synthetic primer

<400> SEQUENCE: 1
ccatcttgtc gtcttcggaa atgtta                                    26

<210> SEQ ID NO 2
<211> LENGTH: 25
<212> TYPE: DNA
<213> ORGANISM: Artificial sequence
<220> FEATURE:
<223> OTHER INFORMATION: Synthetic primer

<400> SEQUENCE: 2
ttgaatgagg caagtcagcc tttct                                     25

<210> SEQ ID NO 3
<211> LENGTH: 21
<212> TYPE: DNA
<213> ORGANISM: Artificial sequence
<220> FEATURE:
<223> OTHER INFORMATION: Synthetic primer

<400> SEQUENCE: 3
cagcctattg cgagagagct g                                         21

<210> SEQ ID NO 4
<211> LENGTH: 21
<212> TYPE: DNA
<213> ORGANISM: Artificial sequence
<220> FEATURE:
<223> OTHER INFORMATION: Synthetic primer

<400> SEQUENCE: 4
gaaaggatct tgggcacttg c                                         21
```